US006207395B1

(12) United States Patent
Valkirs et al.

(10) Patent No.: US 6,207,395 B1
(45) Date of Patent: Mar. 27, 2001

(54) DIAGNOSTIC ASSAYS FOR DETECTION OF ENTAMOEBA HISTOLYTICA

(75) Inventors: Gunars E. Valkirs, Escondido; Joe Buechler, Carlsbad; Jeff Gray, Solano Beach, all of CA (US)

(73) Assignee: Biosite Diagnostics, Inc., San Diego, CA (US)

( * ) Notice: Subject to any disclaimer, the term of this patent is extended or adjusted under 35 U.S.C. 154(b) by 0 days.

(21) Appl. No.: 09/158,347

(22) Filed: Sep. 21, 1998

(51) Int. Cl.[7] .................................................. G01N 33/53
(52) U.S. Cl. .......................... 435/7.22; 435/7.2; 435/7.9; 435/7.92; 435/7.93; 435/7.94; 435/7.95; 435/947; 436/518; 530/388.1; 530/388.8
(58) Field of Search ............................ 435/7.1, 7.2, 7.22, 435/7.9, 7.92, 7.93, 7.94, 7.95, 947; 436/518; 530/388.1, 388.8

(56) References Cited

U.S. PATENT DOCUMENTS

| 4,200,690 | 4/1980 | Root et al. ................................. 435/7 |
| 5,130,417 | 7/1992 | Stanley, Jr. et al. ................. 530/350 |
| 5,272,058 | 12/1993 | Petri, Jr. et al. ..................... 435/7.22 |
| 5,459,042 | 10/1995 | Flores de Castaneda .......... 435/7.22 |

OTHER PUBLICATIONS

Haque et al. "Rapid Diagnosis of Entamoeba Infection by Using Entamoeba *Entamoeba histolytica* Stool Antigen Detection Kits" Journal of Clinical Microbiology, vol. 33, No. 10 (Oct. 1995), pp. 2558–2561. QR46.J87.*

Flores et al. "Serologic Reactivity to Purified Recombinant and Native 29–Kilodalton Peripheral Membrane Protein of Pathogenic *Entamoeba histolytica*" Journal of Clinical Microbiology, vol. 31, No. 6 (Jun. 1993), pp. 1403–1407. QR46.J87.*

Diamond and Clark (1993) *J. Euk. Microbiol.* 40:340–344.

Long and Christie (1995) *Clin. Lab. Med.* 15:307–331.

Healy (1986) *Rev. Infect. Dis.* 8:239–246.

Arvind et al. (1988) *Serodiagn. Immunother. Infect. Dis.* 2:79–81.

Krupp (1970) *Am. J. Trop. Med. Hyg.* 19:57–62.

Lobel et al. (1978) *Ann. Rev. Microbiol.* 32:329–347.

Petri et al. (1989) *J. Biol. Chem.* 264:3007–3012.

Ravdin et al. (1990) *J. Infect. Dis.* 162:768–772.

Mann et al. (1993) *Infect Immun.* 61:1772–1778.

Petri et al. (1990) *Infect. Immun.* 58:1802–1806.

Root et al. (1978) *Arch. Invest. Med.* (Mex) 9:Supplement 1:203.

Haque et al. (1996) 96th ASM General Meeting, New Orleans,LA: TechLab Entamoeba Test and Alexon ProSpecT *Entamoeba histolytica* Microplate Assay.

Torian et al. (1990) *Proc. Nat'l. Acad. Sci. USA* 87:6358–6362.

Bruchhaus and Tannich (1993) *Trop. Med. Parasitol* 44:116–118.

Reed et al. (1992) *Infect. Immun.* 60:542–549.

Tachibana et al. (1991) *J. Clin. Microbiol.* 29:2234–2239.

Soong et al. (1995) *Infect. Immun.* 63:472–477.

* cited by examiner

*Primary Examiner*—Jeffrey Stucker
(74) *Attorney, Agent, or Firm*—Townsend and Townsend and Crew LLP

(57) ABSTRACT

This invention provides methods, reagents, and kits that are useful for diagnosing infection by *E. histolytica*. The methods are based on the discovery of binding agents, including recombinant polyclonal antibodies, that bind to the 29 kDa antigen of *E. histolytica*.

15 Claims, 2 Drawing Sheets

SEQUENCE LISTING

<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:Entamoeba
      histolytica 29 kDa antigen PCR and sequencing
      primer A

<400> SEQUENCE: 1
gtaaaacgac ggccagtgaa ttg                                           23

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence:Entamoeba
      histolytica 29 kDa antigen PCR and sequencing
      primer B

<400> SEQUENCE: 2
acccgttttt ttggatggag tgaaacgatg tcttgcaatc aacaaaaaga g            51

<210> SEQ ID NO 3
<211> LENGTH: 91
<212> TYPE: DNA
<213> ORGANISM: Artificial Sequence
<220> FEATURE:
<223> OTHER INFORMATION: Description of Artificial Sequence:Entamoeba
      histolytica 29 kDa antigen PCR and sequencing
      primer C

<400> SEQUENCE: 3
gtgataaact accgcattaa agcttatcga tgataagctg tcaattagtg atggtgatgg   60
tgatgtagtg ctgttaaata tttcttaatt c                                  91

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Entamoeba
      histolytica 29 kDa antigen PCR and sequencing
      primer D

<400> SEQUENCE: 4
tcgctgccca accagccatg                                               20

<210> SEQ ID NO 5
<211> LENGTH: 75
<212> TYPE: DNA
<213> ORGANISM: Artificial Sequence
<220> FEATURE:
<223> OTHER INFORMATION: Description of Artificial Sequence:Entamoeba
      histolytica 29 kDa antigen PCR and sequencing
      primer E

<400> SEQUENCE: 5
gtgataaact accgcattaa agcttatcga tgataagctg tcaattagtg atggtgatgg   60
tgatgacaat ccctg                                                    75

US 6,207,395 B1

DIAGNOSTIC ASSAYS FOR DETECTION OF ENTAMOEBA HISTOLYTICA

BACKGROUND OF THE INVENTION

1. Field of the Invention

This invention pertains to the field of diagnostic assays for detecting infection of an animal by the protozoan parasite *Entamoeba histolytica*.

2. Background

*Entamoeba histolytica* affects an estimated 480 million people annually; about 10 percent of these people develop colitis, liver abscesses, or other symptoms. Recently, a non-pathogenic species, *E. dispar*, has been described (Diamond and Clark (1993) *J. Euk. Microbiol.* 40: 340–344). *E. dispar* is morphologically identical to the pathogenic species *E. histolytica*.

Diagnosis of *E. histolytica* infection is often difficult. Amoebic dysentery caused by *E. histolytica* is easily confused with monocytic erythrophagocytosis and erythrophagocytosis caused by *Entamoeba coli* (Long and Christie (1995) *Clin. Lab. Med.* 15: 307–331). Early diagnostic assays included microscopy and culture. One more recently developed diagnostic method involves detection of Entamoeba-specific IgG, IgM and IgA antibodies in serum (Healy (1986) *Rev. Infect. Dis.* 8: 239–246; Arvind et al. (1988) *Serodiagn. Inmunother. Infect. Dis.* 2: 79–84). However, seropositivity can persist for years, thus resulting in a high background due to healthy subjects giving positive results (Krupp (1970) *Am. J. Trop. Med. Hyg.* 19: 57–62; Lobel et al. (1970) *Ann. Rev. Microbiol.* 32: 379–347).

Another diagnostic method involves detection of a lectin found on the surface of *E. histolytica* and *E. dispar* trophozoites. Infection of a cell by Entamoeba involves binding of this lectin to Gal/GalNAc residues on the surface of the target cell (Petri et al. (1989) *J. Biol. Clem.* 264: 3007–3012). The lectin, which has a molecular mass of 260 kDa, is composed of two subunits of 170 kDa and 35 kDa. Diagnostic assays that use monoclonal antibodies raised against purified native 170 kDa antigen were found to have problems with false positives (Ravdin et al. (1990) *J. Infect. Dis.* 162: 768–772). Monoclonal antibodies against a recombinantly produced form of the 170 kDa subunit and the use of the antibodies for detecting the 170 kDa antigen are discussed in U.S. Pat. No. 5,272,058 (see also, Mann et al. (1993) *Infect. Immun.* 61: 1772–1778; Petri et al. (1990) *Infect. Immun.* 58: 1802–1806). Other immunoassays for diagnosing *E. histolytica* infection are discussed in, for example, Root et al. (1978) *Arch. Invest. Med.* (Mex) 9: Supplement 1: 203.

Two commercially available immunoassays for *E. histolytica* detection were recently compared to culture and PCR methods (Haque et al. (1996) 96th ASM General Meeting, New Orleans La.). The TechLab "Entamoeba Test" uses a monoclonal antibody to detect a the 170 kDa subunit of the Gal/GalNAc lectin that is present in both pathogenic *E. histolytica* and non-pathogenic *E. dispar*. The Alexon "ProSpecT *Entamoeba histolytica* Microplate Assay" also detects both pathogenic and non-pathogenic Entamoeba species, through use of rabbit polyclonal antisera. Comparison of these two tests to PCR and/or culture methods found that the Alexon test had a sensitivity of only 55% and a correlation of 66%, while the TechLab test had a sensitivity of 100% and a correlation of 84% (Id.). Both tests, however, are unable to distinguish between pathogenic and non-pathogenic strains.

Pathogenic *E. histolytica* trophozoites display a 29 kDa cysteine-rich surface antigen (Torian et al. (1990) Proc. Nat'l Acad. Sci. USA 87: 6358–6362). Monoclonal antibodies raised against this antigen were tested for ability to detect *E. histolytica* infection, but not all clinical isolates were detected (Id.). Thus, a need exists for sensitive and reliable assays for detecting *E. histolytica* infection in a clinical setting. The present invention fulfills this and other needs.

SUMMARY OF THE INVENTION

The present invention provides methods of diagnosing infection of a mammal by an Entamoeba species, in particular *E. histolytica* and *E. dispar*. The methods involve contacting a capture reagent which binds to a 29 kDa antigen of *Entamoeba histolytica* or *Entamoeba dispar* with a stool sample obtained from the mammal. The capture reagent forms a complex with the 29 kDa antigen if the 29 kDa antigen is present in the test sample. The presence or absence of the 29 kDa antigen bound to the capture reagent is then detected; the presence of the 29 kDa antigen is indicative of Eutamoeba infection of the mammal.

The invention also provides devices and kits for diagnosing infection of a mammal by an Entamoeba species, in particular *E. histolytica* and *E. dispar*. The kits typically include, inter alia, a solid support upon which is immobilized a capture reagent which binds to a 29 kDa antigen of *Entamoeba histolytica*, and a detection reagent which binds to the 29 kDa antigen.

Also provided by the invention are recombinant monoclonal and polyclonal antibodies that bind to the 29 kDa antigen.

BRIEF DESCRIPTION OF THE DRAWINGS

FIG. 1A is a top view, showing an elongated well in the center. FIG. 1B is a section view of the top piece, showing a membrane that is ultrasonically welded to the underside of the top piece. FIG. 1C is an end view of the top piece of the apparatus.

FIG. 2A is a top view, FIG. 2B is a section view, and FIG. 2C is an end view of the bottom piece. To construct a complete apparatus, a bottom piece is joined to a top piece such as is shown in FIG. 1A–C.

DETAILED DESCRIPTION

Definitions

Figure 1C:
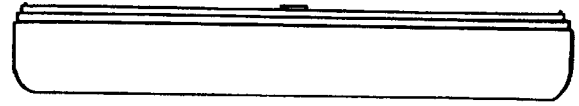
FIGS. 1A–C show a top piece of an apparatus for performing an immunoassay for detecting *E. histolytica* infection in a sample.

The phrases "specifically binds to" or "specifically immunoreactive with", when referring to an antibody or other binding moiety refers to a binding reaction which is determinative of the presence of a target antigen in the presence of a heterogeneous population of proteins and other biologics. Thus, under designated assay conditions, the specified binding moieties bind preferentially to a particular target antigen and do not bind in a significant amount to other components present in a test sample. Specific binding to a target antigen under such conditions may require a binding moiety that is selected for its specificity for a particular target antigen. A variety of immunoassay formats may be used to select antibodies that are specifically immunoreactive with a particular protein. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity. Typically a specific or selective reaction will be at least twice background signal or noise and more typically more than 10 to 100 times background. Specific binding between an antibody or other binding agent and an antigen means a binding affinity of at least $10^6$ M$^{-1}$. Preferred binding agents bind with affinities of at least about $10^7$ M$^-$, and preferably $10^8$ M$^{-1}$ to $10^9$ M$^{-1}$ or $10^{10}$ M$^{-1}$.

The term "epitope" means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-confrontation epitopes are distinguished in that the binding to the former but not the latter is lost in the presence of denaturing solvents.

The basic antibody structural unit is known to comprise a tetramer. Each tetramer is composed of two identical pairs of polypeptide chains, each pair having one "light" (about 25 kDa) and one "heavy" chain (about 50–70 Kda). The amino-terminal portion of each chain includes a variable region of about 100 to 10 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Imnmunology* (See, e.g., Paul, *Fundamental Immunology*, 3$^{rd}$ Ed., 1993, Raven Press, New York).

The variable regions of each light/heavy chain pair form the antibody binding site. The chains all exhibit the same general structure of relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al. (1987) *J. Mol. Biol.* 196: 901–917; (1989) *Nature* 342: 878–883; and (1989) *J. Mol. Biol.* 186: 651–663.

The term "antibody" is used to mean whole antibodies and binding fragments thereof. Binding fragments include single chain fragments, Fv fragments and Fab fragments The term Fab fragment is sometimes used in the art to mean the binding fragment resulting from papain cleavage of an intact antibody. The terms Fab' and F(ab')$_2$ are sometimes used in the art to refer to binding fragments of intact antibodies generated by pepsin cleavage. Here, "Fab" is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. Usually, Fab fragments are formed by complexing a full-length or substantially full-length light chain with a heavy chain comprising the variable domain and at least the CH1 domain of the constant region.

An isolated species or population of species means an object species (e.g., binding polypeptides of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

Description of the Preferred Embodiments

The invention provides methods, reagents, and kits that are useful for diagnosing infection of a mammal by an Entamoeba species, in particular *E. histolytica* and *E. dispar*. The assays provide a rapid, accurate and cost-effective means for detecting Entamoeba infection. The methods of the invention are both sensitive and specific, and can be used for detecting these antigens on the surface of Entamoeba cells, as well as soluble antigens.

The methods, compositions and kits provided by the instant invention are useful for detecting Entamoeba infection in test samples, including biological samples such as cultures, tissue samples, bodily fluids, and the like. Typically, the biological sample analyzed for Entamoeba infection will be a stool sample. For liquid or semi-solid stool samples, a portion of the sample is added to an assay container and, optionally, diluted with a suitable diluent such as water or an appropriate buffer and mixed. Suitable buffers include, for example, buffered protein solutions and the like. Solid stool samples can be placed in a diluent and suspended by vigorous mixing. Typically, the sample is diluted sufficiently to provide a solution of suitable clarity for use in the assays; this is generally about a 3–20 fold dilution, with about a 10-fold dilution being typical. After mixing, one can clarify the sample by, for example, filtration or centrifugation or other methods known to those of skill in the art. In general, well known methods for preparing test samples for assays, such as immunoassays, are suitable for preparing test samples for analysis using the methods provided by the invention.

A. Assay Reagents

The assays of the invention involve detecting the presence of a 29 kDa antigen that is specific for *E. histolytica* and *E. dispar*. The 29 kDa antigen, which encodes an alkyl-hydroperoxidase reductase (Bruchhaus and Tannich (1993) *Trop. Med. Parasitol.* 44: 116–118; Torian et al. (1990) *Proc. Nat'l. Acad. Sci. USA* 87: 6358–6362), is also known as the *E. histolytica* peripheral membrane antigen (Reed et al. (1992) *Infect. Immun.* 60, 542–544; GenBank Accession No. M75858) and the 30 Mr antigen (Tachibana et al. (1991) *J. Clin. Microbiol.* 29: 2234–2239; GenBank Accession No. D00871); these terms are used interchangeably herein.

The invention provides assay reagents that arc capable of specifically binding to the 29 kDa antigen. These assay reagents can be used in one or more steps of the assay. For example, the assay reagents can be immobilized on a solid support and used to immobilize the *E. histolytica* antigens on a solid support. Assay reagents can also be used to detect *E. histolytica* antigens by, for example, attaching a detectable label to a binding moiety that binds to the *E. histolytica* 29 kDa antigen. These are discussed in greater detail below.

The assay means for detecting the *E. histolytica* 29 kDa antigen are, in some embodiments, binding assays. In these assays, which include immunoassays, the 29 kDa antigen is detected using detection reagents that are capable of specifically binding to the 29 kDa antigen. The detection reagents include at least a binding moiety and a detectable label. Suitable binding moieties include any molecule that is capable of specifically binding to the *E. histolytica* 29 kDa antigen. Antibodies and fragments thereof are examples of binding components that are suitable for use in detection moieties.

Various procedures known in the art can be used for the production of antibodies that specifically bind to the 29 kDa antigen. For the production of polyclonal antibodies, one can use the 29 kDa antigen to inoculate any of various host animals, including but not limited to rabbits, mice, rats, sheep, goats, and the like. The 29 kDa antigen can be prepared by recombinant means using an expression vector containing a gene encoding the antigen; the complete nucleotide sequence is available in GenBank, Accession No. X70996.

Monoclonal antibodies can be prepared by any technique that provides for the production of antibody molecules by continuous cell lines in culture, including the hybridoma technique originally developed by Kohler and Milstein ((1975) *Nature* 256: 495–497), as well as the trioma technique, the human B-cell hybridoma technique (Kozbor et al. (1983) *Immunology Today* 4: 72), and the EBV-hybridoma technique to produce human monoclonal antibodies (Cole et al. (1985) in *Monoclonal Antibodies and Cancer Therapy*, Alan R. Liss, Inc., pp. 77–96). Monoclonal antibodies also can be produced in germ-free animals as was described in PCT/US89/02545 (Publication No. WO8912690, published Dec. 12, 1989) and U.S. Pat. No. 5,091,512.

Fragments of antibodies are also useful as binding moieties. While various antibody fragments can be obtained by the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv). Single chain antibodies are also useful to construct detection moieties. Methods for producing single chain antibodies were described in, for example, U.S. Pat. No. 4,946,778. Techniques for the construction of Fab expression libraries were described by Huse et al. (1989) *Science* 246: 1275–1281; these techniques facilitate rapid identification of monoclonal Fab fragments with the desired specificity for the *E. histolytica* 29 kDa antigen. Suitable binding moieties also include those that are obtained using methods such as phage display.

The 29 kDa antigen is found in several allelic forms. Therefore, to ensure that the assay can detect all strains of *E. histolytica*, it is preferred to use a polyclonal preparation of 29 kDa antigen to immunize the animal from which the antibodies are to be obtained. To prepare a suitable antigen preparation, one can prepare a cDNA expression library from *E. histolytica* and screen the library with a polyclonal antibody that is raised against a crude preparation of *E. histolytica* 29 kDa antigen. The cDNA inserts from those expression plasmids that express the 29 kDa antigen are then subcloned and sequenced. Those that encode the different alleles of the 29 kDa antigen are amplified, pooled, and the 29 kDa antigen encoding inserts are cloned into an expression vector and used to transform *E. coli* or other suitable host cells. The resulting preparation of recombinant 29 kDa antigen allelic forms are then used to inoculate an animal, e.g., a mouse.

In preferred embodiments, the assay reagents use recombinantly produced polyclonal or monoclonal antibodies that bind to the *E. histolytica* 29 kDa antigen as binding moieties. Recombinant antibodies are typically produced by immunizing an animal with the 29 kDa antigen, obtaining RNA from the spleen or other antibody-expressing tissue of the animal, making cDNA, amplifying the variable domains of the heavy and light immunoglobulin chains, cloning the amplified DNA into a phage display vector, infecting *E. coli*, expressing the phage display library, and selecting those library members that express an antibody that binds to the 29 kDa antigen. Methods suitable for carrying out each of these steps are described in, for example U.S. patent application Ser. No. 08/835,159, filed Apr. 4, 1997. In preferred embodiments, the antibody or other binding peptides are expressed on the cell surface of a replicable genetic unit, such as a filamentous phage, and especially phage M13, Fd and F1. Most work has inserted libraries encoding polypeptides to be displayed into either gIII or gVIII of these phage, forming a fusion protein which is displayed on the surface of the phage. See, e.g., Dower, WO 91/19818; Devlin, WO 91/18989; MacCafferty, WO 92/01047 (gene III); Huse, WO 92/06204; Kang, WO 92/18619 (gene VIII).

In a preferred embodiment, the genes that encode the heavy and light chains of antibodies present in the cDNA library are amplified using a set of primers that can amplify substantially all of the different heavy and light chains. The resulting amplified fragments that result from the amplification step are pooled and subjected to asymmetric PCR so that only one strand (e.g., the antisense strand) is amplified. The single strand products are phosphorylated, annealed to a single-stranded uracil template (e.g., the vector BS45, described in U.S. patent application Ser. No. 08/835,159, which has coding regions for the constant regions of mouse heavy and light chains), and introduced into a uracil DNA glycosylase$^+$ host cell to enrich for vectors that contain the coding sequences for heavy and light chain variable domains.

To screen for phage that express an antibody that binds to the 29 kDa antigen, one can attach a label to the 29 kDa antigen using methods known to those of skill in the art. In a preferred embodiment, the phage that display such antibodies are selected using a 29 kDa antigen to which is attached an immobilizable tag, e.g., biotin. The phage are contacted with the biotinylated antigen, after which the phage are selected by contacting the resulting complex with avidin attached to a magnetic latex bead or other solid support. The selected phage are then plated, and may be screened with the 29 kDa antigen to which is attached a detectable label.

In a preferred embodiment, the library is enriched for those phage that display more than one antibody that binds to the 29 kDa antigen. Methods and vectors that are useful for this enrichment are described in U.S. patent application Ser. No. 08/835,159. The panning can be repeated one or more times to enhance the specificity and sensitivity of the resulting antibodies. Preferably, panning is continued until the percentage of functional positives is at least about 70%, more preferably at least about 80%, and most preferably at least about 90%.

A recombinant anti-29 kDa antigen monoclonal antibody can then be selected by amplifying antibody-encoding DNA from individual plaques, cloning the amplified DNA into an expression vector, and expressing the antibody in a suitable host cell (e.g., *E. coli*). The antibodies are then tested for ability to bind the *E. histolytica* 29 kDa antigen. An example of a recombinant monoclonal antibody prepared using this method is the mAb EH29.Ab.13, which was deposited under the Budapest Treaty with the American Type Culture Collection (10801 University Boulevard, Manassas, Va. 20110-2209) on Sep. 1, 1998, and have been assigned ATCC Accession No. 98856.

Recombinant polyclonal antibodies are particularly preferred, in particular because of the various allelic forms of the *E. histolytica* 29 kDa antigen. The diverse fine binding specificity of members of a population of polyclonal antibodies often allows the population to bind to several variant forms of the 29 kDa antigen (e.g., species variants, escape mutant forms) to which a monoclonal reagent may be unable to bind. Methods for producing recombinant polyclonal antibodies are described in co-pending, commonly assigned U.S. patent application Ser. No. 08/835,159, filed Apr. 4, 1997. Specific methods of producing recombinant polyclonal antibodies that bind to the 29 kDa antigen are described in the Examples below.

Polyclonal antibodies can be prepared as described above, except that an individual antibody is not selected. Rather, the pool of phage are used for the screening, preferably using an equal number of phage from each sample. In preferred embodiments, the phage are enriched for those that display more than one copy of the respective antibodies. The phage are then selected for those that bind to a mixture of 29 kDa antigen allelic variants. For example, one can use a biotinylated anti-29 kDa antigen monoclonal antibody and a pool of allelic variants of 29 kDa antigen to concentrate those phage that express antibodies that bind to the 29 kDa antigen. The biotinylated monoclonal antibody is immobilized on a solid support (e.g., magnetic latex) to which is attached avidin. The phage that are bound to the immobilized 29 kDa antigen are eluted, plated, and the panning repeated until the desired percentage of functional positives is obtained.

B. Assay Formats

The assays for detecting *E. histolytica* infection can be performed in any of several formats. For example, a sandwich assay can be performed by preparing a biological sample as discussed above, or as is otherwise appropriate for the particular sample, and placing the sample in contact with a solid support on which is immobilized a plurality of capture reagents that bind the 29 kDa antigen. The 29 kDa antigen, if present in the sample, binds to the capture reagents. The solid support is then contacted with detection reagents for the 29 kDa antigen. The solid support can be washed prior to contact with detection reagents to remove unbound reagents. After incubation of the detection reagents for a sufficient time to bind a substantial portion of the immobilized 29 kDa antigen, any unbound labeled reagents are removed by, for example, washing. The detectable label associated with the detection reagents is then detected. For example, in the case of an enzyme used as a detectable label, a substrate for the enzyme that turns a visible color upon action of the enzyme is placed in contact with the bound detection reagent. A visible color will then be observed in proportion to the amount of the specific antigen in the sample.

The capture reagent can be any compound that specifically binds to the 29 kDa antigen. Examples of binding moieties that are suitable for use as capture reagents are described above. One example of a suitable capture reagent is the recombinant polyclonal antibody EH29.Ab.32.PC, which was prepared as described in the Examples. Cells that produce these recombinant polyclonal antibodies were deposited under the Budapest Treaty with the American Type Culture Collection (10801 University Boulevard, Manassas, Va. 20110-2209) on Sep. 1, 1998, and have been assigned ATCC Accession No. 98855.

To immobilize the 29 kDa antigen on the solid support, a capture reagent that specifically binds to the 29 kDa antigen is non-diffusively associated with the support. The capture reagents can be non-diffusively immobilized on the support either by covalent or non-covalent methods, which are known to those of skill in the art. See, e.g., Pluskal et al. (1986) *BioTechniques* 4: 272–283. Suitable supports include, for example, glasses, plastics, polymers, metals, metalloids, ceramics, organics, and the like. Specific examples include, but are not limited to, microtiter plates, nitrocellulose membranes, nylon membranes, and derivatized nylon membranes, and also particles, such as agarose, SEPHADEX™, and the like. Assay systems for use in the methods and kits of the invention include, but are not limited to, dipstick-type devices, immunochromatographic test strips and radial partition immunoassay devices, and flow-through devices. Conveniently, where the solid support is a membrane, the sample will flow through the membrane, for example, by gravity, capillary action, or under positive or negative pressure.

Preferred assay systems for use in the kits and methods of the invention are described in EP 447154. These systems employ an apparatus that includes a porous member such as a membrane or a filter onto which is bound a multiplicity of anchor moieties for the 29 kDa antigen. The apparatus also includes a non-absorbent member with a textured surface in communication with the lower surface of the porous member. The textured surface of the non-absorbent member can be a grooved surface such as the surface of a record or it can be composed of channels, such that when the porous and non-absorbent members are brought into contact with one another a network of capillary channels is formed. The capillary network is formed from the contact of the porous member with the textured surface of the non-absorbent member and can be constructed either before or subsequent to the initial contacting of the porous member with a fluid. In some embodiments, the capillary communication between the porous member and the non-absorbent member favors delaying the transferal of fluid from the porous member to the capillary network formed by the porous member and the textured surface of the non-absorbent member until the volume of the added fluid substantially exceeds the void volume of the porous member. The transferal of fluid from the porous member to the network of capillary channels formed by the porous member and the textured surface of the non-absorbent member can occur without the use of external means, such as positive external pressure or vacuum, or contact with an absorbent material. The devices of the present invention can also include an optional member which is placed in contact with the upper surface of the porous member and may be used to partition the upper surface of the device into discrete openings. Such openings can access either the porous member or the textured surface of the non-absorbent second member. The optional member can in conjunction with the non-absorbent member compose a fluid receiving zone in which there is no intervening porous member. A fluid receiving zone constructed from the non-absorbent member and the optional member provides fluid capacity in addition to that provided by the network of capillary channels created by the contact of the porous member and the non-absorbent member. The openings in the optional member may include a first fluid opening and also an additional fluid opening. The first fluid opening functions as a portal for the introduction of the first fluid added to the device. The additional fluid opening serves as an additional portal through which additional fluids may be added to the inventive device.

To perform an assay using these devices, a volume of the sample is added to the porous member, where the sample permeates the void volume of the porous member and thereby contacts the anchor moieties immobilized on the porous member. In a non-competitive assay, the sample to be assayed is applied to the porous member and the *E. histolytica* 29 kDa antigen, if present, is bound by the anchor moieties. A detection reagent for the 29 kDa antigen is then added as an additional fluid; these bind to the complex of 29 kDa antigen and capture reagent. Alternatively, the detection reagent can be added to the sample prior to application of the sample to the porous member so that the binding of detection reagent to the 29 kDa antigen occurs prior to the binding of 29 kDa antigen to the capture reagent. In another embodiment, the capture reagent and detection reagent are added to the sample, after which the complex of capture reagent, 29 kDa antigen, and detection reagent binds to a binding agent that is either combined with these reagents or is immobilized on the porous member. An additional fluid containing reagents to effect a separation of free from bound labeled reagents can be added to remove excess detection reagent, if needed.

This device is designed to provide sufficient sensitivity to measure low concentrations of *E. histolytica* 29 kDa antigen because one can use large amounts of sample and efficiently remove the excess of detection reagent. Indeed, the efficient separation of free from bound label achieved by the network of capillary channels of this device improves the discrimination of specific 29 kDa antigen-associated signal over non-specific background signal. If needed, a signal developer solution is then added to enable the label of the detection moiety to develop a detectable signal. The signal developed can then be related to the concentration of the target ligand within the sample. In a preferred embodiment, the transfer of fluid between the porous first member of the device and the network of capillary channels formed by the contact of the porous member and textured surface of the non-absorbent second member of the device is generally self-initiated at the point when the total volume of fluid added to the device exceeds the void volume of the porous member, thus obviating the need for active interaction by the user to remove excess fluid from the analyte detection zone. The point at which the fluid transfer is initiated is dependent upon the objectives of the assay. Normally, it is desirable to contact the sample with all of the zones on the porous member which contain immobilized receptor. This method enables the detection of the 29 kDa antigen in a manner that is simple, rapid, convenient, sensitive and efficient in the use of reagents.

Competitive binding assays can also be used to detect *E. histolytica* 29 kDa antigen. Conveniently, these assays are performed using the described devices by adding to a sample a labeled analog of the 29 kDa antigen. The labeled analog and *E. histolytica* 29 kDa antigen present in the sample compete for the binding sites of the capture reagents. Alternatively, the capture reagents can be combined with the sample and labeled analogs with subsequent immobilization of the capture reagents onto the porous member through contact with a binding agent. An additional fluid to separate the free from bound label may be added to the device, followed if needed by a signal development solution to enable detection of the label of the labeled analog which has complexed with capture reagent immobilized on the porous member. The amount of labeled *E. histolytica* 29 kDa antigen bound to the porous member is related to the concentration of 29 kDa antigen in the sample.

This invention also provides kits for the detection and/or quantification of *E. histolytica* 29 kDa antigen by the described methods. The kits can include a container containing one or more of the above-discussed detection reagents with or without labels, and capture reagents, either free or bound to solid supports. Also included in the kits can be a suitable membrane, preferably in the form of an assay apparatus that is adapted to use in the described assay. Preferably, the kits will also include reagents used in the described assays, including reagents useful for detecting the presence of the detectable labels. Other materials useful in the performance of the assays can also be included in the kits, including test tubes, transfer pipettes, and the like. The kits can also include written instructions for the use of one or more of these reagents in any of the assays described herein.

The kits of the invention can also include an internal and/or an external control. An internal control can consist of the 29 kDa antigen. The control antigen can conveniently be preattached to a capture reagent in a zone of the solid support adjacent to the zone to which the sample is applied. The external control can also consist of the 29 kDa antigen. Typically, the antigen present in the external control will be at a concentration at or above the sensitivity limit of the assay means. The external control antigen can be diluted in the sample diluent and assayed in the same manner as would a biological sample. Alternatively, the external control 29 kDa antigen can be added to an aliquot of an actual biological sample to determine the sensitivity of the assay. The kits of the present invention can contain materials sufficient for one assay, or can contain sufficient materials for multiple assays.

The methods, compositions and kits provided by the invention are capable of detecting the *E. histolytica* 29 kDa antigen with high sensitivity. The assays and kits will detect *E. histolytica* 29 kDa antigen when present in a sample at a concentration of about 100 ng/ml or less. Preferably, the detection limit for 29 kDa antigen will be about 20 ng/ml or less, more preferably about 4 ng/ml or less, and still more preferably the detection limit for 29 kDa antigen will be about 1 ng/ml or less.

C. Detection Reagents

The presence of *E. histolytica* 29 kDa antigen is generally detected using a detection reagent that is composed of a binding moiety that specifically binds to the 29 kDa antigen. The detection reagents are either directly labeled, i.e., comprise or react to produce a detectable label, or are indirectly labeled, i.e., bind to a molecule comprising or reacting to produce a detectable label. Labels can be directly attached to or incorporated into the detection reagent by chemical or recombinant methods.

In one embodiment, a label is coupled to a molecule, such as an antibody that specifically binds to the *E. histolytica* 29 kDa antigen, through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. Preferred linkers are often flexible amino acid subsequences which are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the assays of the present invention, which are attached to the detection reagent, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) *Introduction to Immunocytochemistry,* 2nd ed., Springer Verlag, N.Y. and in Haugland (1996) *Handbook of Fluorescent Probes and Research Chemicals,* a combined handbook and catalogue Published by Molecular Probes, Inc., Eugene, OR. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

For use of the present invention in the clinic, preferred labels are non-radioactive and readily detected without the necessity of sophisticated instrumentation. Preferably, detection of the labels will yield a visible signal that is immediately discernable upon visual inspection. One preferred example of detectable secondary labeling strategies uses an antibody that recognizes *E. histolytica* 29 kDa antigen in which the antibody is linked to an enzyme (typically by recombinant or covalent chemical bonding). The antibody is detected when the enzyme reacts with its substrate, producing a detectable product. Preferred enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

EXAMPLES

The following examples are offered to illustrate, but not to limit the present invention.

Example 1

Immunization of Rabbits with Crude *Entamoeba histolytica* Antigen

*Entamoeba histolytica,* ATCC strain 30885, was cultured in Diamond's TYI-S-33 medium (Diamond, L. S., Harlow, D. R., and Cunnick, C. C., Trans. R. Soc. Trop. Med. Hyg. 72:431–432, 1978) supplemented with 10% heat-inactivated adult bovine serum (Biofluids, Inc., Rockville, Md.). A culture of *Entamoeba histolytica* trophozoites strain #30885 (approximately $7 \times 10^7$ organisms) was subjected to centrifugation in an IEC tabletop centrifuge at 3,500 rpm for 30 min at 4° C. The pellet was washed twice by completely resuspending it in ice-cold, sterile PBS (phosphate buffered saline) and centrifuging as above. After the final wash, the pellet was resuspended in 28 ml of sterile PBS in a 50 ml disposable sterile centrifuge tube. The sample was placed on ice and sonicated using a Braun-Sonic U sonicator (B. Braun Biotech, Allentown, Pa.) set at 200 watts for 5×15 sec with a 15 sec rest in between bursts to ensure that the sample remained ice-cold. The crude *E. histolytica* antigen sample was aliquoted into screw top tubes on liquid nitrogen and stored at −80° C. The sample was estimated to contain 2.5 mg/ml protein. Rabbits were immunized by Antibodies Inc. (Davis, Calif.) with the crude *Entamoeba histolytica* antigen preparation following standard protocols. The rabbit anti-*Entamoeba histolytica* polyclonal was designated antibody #588.

Example 2

Generation and Screening of *E. histolytica* cDNA Libraries

This Example describes the cloning of cDNAs that encode the 29 kDa antigen of *E. histolytica.*

A. Isolation and purification of RNA from *Entamoeba histolytica* trophozoites

Messenger RNA (mRNA) was purified from *E. histolytica* trophozoites (strain 30887) using an Oligotex™ direct mRNA isolation kit (Qiagen, Santa Clarita, Calif.) according to the manufacturer's recommendations. The concentration was determined by $A_{260}$ using an absorbance of 1.0 for a concentration of 33 µg/ml. The mRNA was stored at −80° C.

B. Synthesis of Lambda cDNA libraries

The mRNA (5.0 μg) purified above was used to synthesize the first and second strands of cDNA using a cDNA synthesis kit (Stratagene, San Diego, Calif.) following the manufacturer's recommendations. The resulting cDNA was selected for inserts greater than 500 base pairs in length. The size-selected cDNA was then ligated into the Uni-ZAP XR™ vector (Stratagene, San Diego, Calif.) and packaged with Gigapak Gold™ packaging extract (Stratagene, San Diego, Calif.) following the manufacturer's recommendations. The primary library size of $2.6 \times 10^6$ plaque-forming units (pfu) was determined by plating serial dilutions of the packaged library (see below). Background was determined to be approximately 2% through blue/white selection (see below). The resulting Uni-ZAP XR™ lambda phage library was amplified once before screening to ensure stability of the library, titered, and stored at 4° C.

C. Plating Lambda phage cDNA library

Starting with a lambda phage stock, a series of 100-fold dilutions (10 μl to 1.0 ml) were made in SM buffer (Stratagene, San Diego, Calif.). The diluted phage samples (10 μl) were added to 200 μl of an overnight culture of *Escherichia coli* strain XL1-Blue™ MRF' (Stratagene, San Diego, Calif.) adjusted to $OD_{600}$=0.5 in 10 mM $MgSO_4$ in sterile 15ml tubes and incubated at 37° C. for 15 min. After adding 3.0 ml of NZY top-agar (top agar stored at 55° C., Appendix A1, Sambrook et al., *Molecular Cloning, A Laboratory Manual* (1989)), the mixture was evenly distributed on an NZY agar plate (100 mm, Appendix A1, Sambrook et al., supra.) that had been pre-warmed (37° C.–55° C.) to remove any excess moisture on the agar surface. The plates were cooled to room temperature. When the top-agar had solidified, the plates were inverted and placed at 37° C. overnight. The number of plaques was then counted to determine the titer.

In order to determine the background for the library (the percentage of clones not carrying an insert), several hundred plaques were plated as described above. Prior to plating, 15μl of 0.5M isopropyl-β-D-thiogalactoside (IPTG) and 50 μl of 5-bromo-4-chloro-3-indoyl-β-d-galctopyranoside (X-gal) [250 mg/ml (in dimethylformamide)] was added to the NZY top agar. These plates were incubated at 37° C. for 6–8 hours and transferred to room temperature overnight. Plaques that stained blue correspond to clones that do not have an insert, while non-staining, white plaques contain an insert. The percentage of background plaques was calculated to be 3 percent by dividing the number of blue plaques by the total number of plaques.

D. Screening of *E. histolytica* trophozoite cDNA library with polyclonal antibody and identification of 29 kDa antigen The *Entamoeba histolytica* trophozoite cDNA library was plated on 150 mm NZY agar plates at a density of approximately 10,000–20,000 pfu/plate as described above, except that 600 μl of $OD_{600}$=0.5 XL1-Blue cells and nine ml of NZY top agar were used for plating. When the plaques reached 0.5–1.0 mm in diameter (4–5 hr), nitrocellulose filters (pore size 0.45 μm, BA85 Protran, Schleicher and Schuell, Keene, N.H.) that had been soaked in 10 mM isopropyl-β-D-thiogalactoside (IPTG) were placed on the agar plates, marked asymmetrically with a needle, and incubated at 20° C.

After overnight incubation, the filters were carefully removed from the plates with membrane forceps, rinsed briefly in TBST (40 mM TRIS (pH 7.5), 150 mM NaCl, 0.05% Tween 20 (Fisher Chemical, Pittsburgh, Pa.)) to remove any debris from the lifts, and incubated for greater than 1 hr in blocking solution (1% BSA solution containing 20 mM TRIS (pH 8.0), 150 mM NaCl, and 0.1% sodium azide). The filters were then incubated in rabbit anti-*Entamoeba histolytica* trophozoite polyclonal (Example 1) diluted 1/500–1/1000 in blocking solution for a minimum of 4 hours. The filters were washed twice with TBST for 2 min each and placed in goat anti-rabbit (H+L)-AP (Southern Biotechnology Associates, Inc, Birmingham, Al.) diluted 1/1000 in blocking solution for one hour. Filters were washed three times with TBST for five minutes each.

After the final wash, the filters were developed as described in Example 13. The filters were aligned with the agar plates through the asymmetric needle marks and plaques individually cored from the agar plates and transferred to 250–500 μl of SM buffer. The plaques were chosen based on their staining intensity with the rabbit anti-*E. histolytica* polyclonal, ranging from light staining to dark staining. These plaques were purified to homogeneity through iterative rounds of the plating/filter lift procedure described above.

The DNA inserts were subcloned into the plasmid vector pBluescript (Stratagene, San Diego, Calif.) through an in vivo excision process following the manufacturer's recommendations. The 3' DNA sequence of each clone was determined by the dideoxy chain termination method using Sequenase™ II DNA cloning kit (U.S. Biochemical) and an oligonucleotide primer (A, Table 1) that binds to the DNA sequence on the 3' side of the insert in the pBluescript vector. A total of 69 clones were sequenced from this library of which 16 (23%) corresponded to the published sequence for the *Entamoeba histolytica* 29 kDa antigen (Soong et al. (1995) *Infect. Immun.* 63: 472–477).

TABLE 1

| | PCR and Sequencing Primer Sequences | |
|---|---|---|
| A: | 5'-GTAAAACGACGGCCAGTGAATTG-3' | (SEQ ID NO: 1) |
| B: | 5'ACCCGTTTTTTTGGATGGAGTGAAACGATGTCTTGCAATCAACAAAAAGAG-3' | (SEQ ID NO: 2) |
| C: | 5'-GTGATAAACTACCGCATTAAAGCTTATCGATGATAAGCTGTCAATTAGTGATGGTGATGGTGATGTAGTGCTGTTAAATATTTCTTAATTC-3' | (SEQ ID NO: 3) |
| D: | 5'-TCGCTGCCCAACCAGCCATG-3' | (SEQ ID NO: 4) |
| E: | 5'-GTGATAAACTACCGCATTAAAGCTTATCGATGATAAGCTGTCAATTAGTGATGGTGATGGTGATGACAATCCCTG-3' | (SEQ ID NO: 5) |

Example 3

Cloning of Polyclonal *Entamoeba histolytica* 29 kDa Antigen

PCR primers were made corresponding to the coding sequence at the 5'-end of 29 kDa antigen and the coding sequence at the 3'-end of the 29 kDa antigen (primers B and C respectively, Table 1). The 3' primer also had six histidine codons inserted between the end of the coding sequence of the 29 kDa antigen and the stop codon to assist in purification of the recombinant protein by metal-chelate chromatography. In addition, the 5' primer contains 20 base pairs of vector sequence at its 5'-end corresponding to the 3'-end of the pBRnsiH3 vector (described in copending, commonly assigned U.S. patent application Ser. No. 08/835,159, filed Apr. 4, 1997). The 3' primer contains the 19 base pairs of the tet promoter removed by HindIII digestion, in addition to 20 base pairs of vector sequence 3' to the HindIII site at its 5' end (see, Example 17 of U.S. patent application Ser. No. 08/835,159).

The polyclonal antigen was cloned from the cDNA library because there are regions of the cDNA sequences showing allelic variations (Reed et al. (1992) Infect. Immun. 60: 542–549). The 29 kDa insert was amplified with the primers described above using 5 μl E. histolytica unamplified cDNA library as template per reaction. The DNA insert was amplified (3×100 μl reactions) with Expand™ DNA polymerase, and the reactions were pooled and purified as generally described in Example 19 of U.S. patent application Ser. No. 08/835,159, filed Apr. 4, 1997. The 29 kDa insert was annealed with the pBRnsiH3 at a 3:1 molar excess of insert to vector, and an aliquot electroporated into 40 μl of electrocompetent E. coli strain, DH10B as described in Example 11. The transformed cells were diluted to 1.0 ml with 2xYT and allowed to recover at 37° C. for one hr. The culture was diluted 1/100 into 30 ml 2xYT supplemented with 1% glycerol and tetracycline (20kg/ml) and grown overnight at 37° C. at 300 rpm. After the overnight incubation, 0.3 ml of culture was diluted into 30 ml 2xYT supplemented with 1% glycerol and tetracycline (20 μg/ml) and grown for 8 hr at 300 rpm and 37° C. Glycerol freezer stocks were made from this culture for long-term storage at −80° C. The 29 kDa antigen was expressed and purified as described in Example 4.

Example 4

Expression and Purification of Recombinant Antibodies and E. histolytica 29 kDa Antigen This Example describes the expression of the E. histolytica 29 kDa antigen, as well as recombinant antibodies that bind to this antigen, using recombinant E. coli cells that contain genes encoding the 29 kDa antigen of E. histolytica or antibodies against this antigen.

A. Expression and purification of recombinant antibodies

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium (Pack et al. (1993) Bio/Technology 11: 1271–1277) supplemented with 3 g/L L-leucine, 3 g/L L-isoleucine, 12 g/L casein digest (Difco, Detroit, Mich.), 12.5 g/L glycerol and 10 μg/ml tetracycline. The temperature, pH and dissolved oxygen in the fermentor were controlled at 26° C., 6.0–6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following rim termination and adjustment of pH to 6.0, the culture was passed twice through an M-21 OB-EH Microfluidizer (Microfluidics, Newton, Mass.) at 17000 psi. The high pressure homogenization of the cells releases the Fab into the culture supernatant.

The first step in purification was expanded bed immobilized metal affinity chromatography (EB-IMAC). Streamline Chelating resin (Pharmacia, Piscataway, N.J.) was charged with 0.1 M $NiCl_2$ and was then expanded and equilibrated in 50 mM acetate, 200 mM NaCl, 10 mM imidazole, 0.01% $NaN_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passes through unhindered, but the Fab is captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% $NaN_3$, pH 8.0 buffer flowing in the downward direction.

The second step in the purification used ion-exchange chromatography (IEC). Q Sepharose FastFlow resin (Pharmacia, Piscataway, N.J.) was equilibrated in 20 mM borate, 37.5 mM NaCl, 0.01% $NaN_3$, pH 8.0. The Fab elution pool from the EB-IMAC step was diluted four-fold in 20 mM borate, 0.01% $NaN_3$, pH 8.0 and loaded onto the IEC column. After washing, the Fab was eluted with a 37.5–200 mM NaCl salt gradient. The elution fractions were evaluated for purity using an Xcell II SDS-PAGE system (Novex, San Diego, Calif.) prior to pooling. Finally, the Fab pool was concentrated and diafiltered into 20 mM borate, 150 mM NaCl, 0.01% $NaN_3$, pH 8.0 buffer for storage. This was achieved in a Sartocon Slice system fitted with a 10,000 MWCO cassette (Sartorius, Bohemia, N.Y.). The final purification yields are typically 50%. The concentration of the purified Fab is measured by UV absorbance at 280 nm, assuming an absorbance of 1.6 for a 1 mg/mL solution.

B. Expression and purification of 29 kDa antigen

A shake flask inoculum was generated overnight from a −70° C. cell bank in an incubator shaker set at 37° C., 300 rpm. The cells were cultured in a defined medium described above. The inoculum was used to seed a 2 L Tunair shake flask (Shelton Scientific, Shelton, Conn.) which was grown at 37° C., 300 rpm. Expression was induced by addition of L(+)-arabinose to 2 g/L during the logarithmic growth phase, following which, the flask is maintained at 23° C., 300 rpm. Following batch termination, the culture is passed through an M-110Y Microfluidizer (Microfluidics, Newton, Mass.) at 17000 psi. The homogenate is clarified in a J2-21 centrifuge (Beckman, Fullerton, Calif.).

Purification employed immobilized metal affinity chromatography. Chelating Sepharose FastFlow resin (Pharmacia, Piscataway, N.J.) was charged with 0.1 M $NiCl_2$ and equilibrated in 20 mM borate, 150 mM NaCl, 10 mM imidazole, 0.01% $NaN_3$, pH 8.0 buffer. A stock solution was used to bring the culture supernatant to 10 mM imidazole and 2-mercaptoethanol was added to 1 mM. The culture supernatant was then mixed with the resin and incubated in the incubator shaker set at room temperature, 150–200 rpm. The antigen was captured by means of the high affinity interaction between nickel and the hexahistidine tag on the antigen. The culture supernatant and resin mixture is poured into a chromatography column. After washing, the antigen was eluted with 20 mM borate, 150 mM NaCl, 200 mM imidazole, 1 mM 2-mercaptoethanol, 0.01% $NaN_3$, pH 8.0 buffer. The antigen pool was concentrated in a stirred cell fitted with a 10,000 MWCO membrane (Amicon, Beverly, Mass.). It was then dialyzed overnight into 20 mM borate, 150 mM NaCl, 0.01% NaN$_3$, pH 8.0 for storage, using 12–14,000 MWCO dialysis tubing. The purified antigen was evaluated for purity by SDS-PAGE analysis. The concentration of the 29 kDa antigen is based on UV absorbance at 280 nm, assuming an absorbance of 1.2 for a 1 mg/mL solution. Antibody shake flask expression and purification is done as described for antigen.

Example 5

Immunization of Mice with Recombinant Antigen and Purification of RNA from Mouse Spleens Mice were immunized by the following method based on experience of the timing of spleen harvest for optimal recovery of mRNA coding for antibody. Two species of mice were used: Balb/c (Charles River Laboratories, Wilmington, Mass.) and A/J (Jackson Laboratories, Bar Harbor, Me). Mice were immunized intraperitoneally or subcutaneously with antigen using 50–100 µg protein in Freund's complete adjuvant on day 0, and day 28. Tests bleeds of mice were obtained through puncture of the retro-orbital sinus. If, by testing the titers, they were deemed high by ELISA using biotinylated antigen immobilized via streptavidin, the mice were boosted with 50 µg of protein on day 70, 71 and 72, with subsequent sacrifice and splenectomy on day 77. If titers of antibody were not deemed satisfactory, mice were boosted with 50 µg antigen on day 56 and a test bleed taken on day 63. If satisfactory titers were obtained, the animals were boosted with 50 µg of antigen on day 98, 99, and 100 and the spleens harvested on day 105.

The spleens were harvested in a laminar flow hood and transferred to a petri dish, trimming off and discarding fat and connective tissue. The spleen was, working quickly, macerated with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)). The spleen suspension was pulled through an 18 gauge needle until viscous and all cells were lysed, then transferred to a microcentrifuge tube. The petri dish was washed with 100 µl of solution D to recover any remaining spleen cells, and this wash was transferred to the tube. The suspension was then pulled through a 22 gauge needle an additional 5–10 times.

The sample was divided evenly between two microcentrifuge tubes and the following added, in order, with mixing by inversion after each addition: 100 µl 2 M sodium acetate (pH 4.0), 1.0 ml water-saturated phenol (Fisher Scientific, Pittsburgh, Pa.), 200 µl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2–8° C., the aqueous phase was transferred to a fresh tube. An equal volume of water saturated phenol/chloroform/isoamyl alcohol (50:49:1) was added, and the tube was vortexed for ten seconds. After a 15 min incubation on ice, the sample was centrifuged for 20 min at 2–8° C., and the aqueous phase was transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed.

The RNA pellets were each dissolved in 300 µl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 µl of ice-cold 70% ethanol. The sample was again centrifuged 14 krpm for 20 min at 4° C., the 70% ethanol solution aspirated, and the RNA pellet dried in vacuo. The pellet was resuspended in 100 µl of sterile distilled water. The concentration was determined by A$_{260}$ using an absorbance of 1.0 for a concentration of 40 µg/ml. The RNA was stored at −80° C.

Example 6

Preparation of Complementary DNA (cDNA)

The total RNA purified as described above was used directly as template for cDNA. RNA (50 µg) was diluted to 100 µL with sterile water, and 10 µL of 130 ng/µL oligo dT$_{12}$ (synthesized on Applied Biosystems Model 392 DNA synthesizer) was added. The sample was heated for 10 min at 70° C., then cooled on ice. Forty µL 5X first strand buffer was added (Gibco/BRL, Gaithersburg, Md.), along with 20 µL 0.1 M dithiothreitol (Gibco/BRL, Gaithersburg, Md.), 10 µL 20 mM deoxynucleoside triphosphates (dNTP's, Boehringer Mannheim, Indianapolis, Ind.), and 10 µL water on ice. The sample was then incubated at 37° C. for 2 min. Ten µL reverse transcriptase (Superscript™ II, Gibco/BRL, Gaithersburg, Md.) was added and incubation was continued at 37° C. for 1 hr. The cDNA products were used directly for polymerase chain reaction (PCR).

Example 7

Amplification of cDNA by PCR

To amplify substantially all of the H and L chain genes using PCR, primers were chosen that corresponded to substantially all published sequences. Because the nucleotide sequences of the amino terminals of H and L contain considerable diversity, 33 oligonucleotides were synthesized to serve as 5' primers for the H chains, and 29 oligonucleotides were synthesized to serve as 5' primers for the kappa L chains as described in co-pending, commonly assigned U.S. patent application Ser. No. 08/835,159, filed Apr. 4, 1997. The constant region nucleotide sequences required only one 3' primer each to the H chains and the kappa L chains. Id.

Amplification by PCR was performed separately for each pair of 5' and 3' primers. A 50 µL reaction was performed for each primer pair with 50 pmol of 5' primer, 50 pmol of 3' primer, 0.25 µL Taq DNA Polymerase (5 units/µL, Boehringer Mannheim, Indianapolis, Ind.), 3 µL cDNA (prepared as described in Example 6), 5 µL 2 mM dNTP's, 5 µL 10×Taq DNA polymerase buffer with MgCl$_2$ (Boehringer Mannheim, Indianapolis, Ind.), and H$_2$O to 50 µL. Amplification was done using a GeneAmp® 9600 thermal cycler (Perkin Elmer, Foster City, Calif.) with the following program: 94° C. for I min; 30 cycles of 94° C. for 20 sec, 55° C. for 30 sec, and 72° C. for 30 sec; 72° C. for 6 min; 4° C.

The dsDNA products of the PCR process were then subjected to asymmetric PCR using only a 3' primer to generate substantially only the anti-sense strand of the target genes. A 100 µL reaction was done for each dsDNA product with 200 pmol of 3' primer, 2 µL of ds-DNA product, 0.5 µL Taq DNA Polymerase, 10 µL 2 mM dNTP's, 10 µL 10 X Taq DNA polymerase buffer with MgCl$_2$ (Boehringer Mannheim, Indianapolis, Ind.), and H$_2$O to 100 µL. The same PCR program as that described above was used to amplify the single-stranded (ss)-DNA.

Example 8
Purification of ss-DNA by High Performance Liquid Chromatography and Kinasing ss-DNA The H chain ss-PCR products and the L chain ss-PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2–8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 μL water and the L chain products were pooled separately in 210 μL water. The ss-DNA was purified by high performance liquid chromatography (HPLC) using a Hewlett Packard 1090 HPLC and a Gen-Pak™ FAX anion exchange column (Millipore Corp., Milford, Mass.). The gradient used to purify the ss-DNA is shown in Table 2, and the oven temperature was at 60° C. Absorbance was monitored at 260 nm. The ss-DNA eluted from the HPLC was collected in 0.5 min fractions. Fractions containing ss-DNA were ethanol precipitated, pelleted and dried as described above. The dried DNA pellets were pooled in 200 μL sterile water.

TABLE 2
HPLC gradient for purification of ss-DNA

| Time (min) | % A | % B | % C | Flow (mL/min) |
| --- | --- | --- | --- | --- |
| 0 | 70 | 30 | 0 | 0.75 |
| 2 | 40 | 60 | 0 | 0.75 |
| 32 | 15 | 85 | 0 | 0.75 |
| 35 | 0 | 100 | 0 | 0.75 |
| 40 | 0 | 100 | 0 | 0.75 |
| 41 | 0 | 0 | 100 | 0.75 |
| 45 | 0 | 0 | 100 | 0.75 |
| 46 | 0 | 100 | 0 | 0.75 |
| 51 | 0 | 100 | 0 | 0.75 |
| 52 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The ss-DNA was phosphorylated on the 5' end in preparation for mutagenesis (Example 10). Twenty-four μL 10×kinase buffer (United States Biochemical, Cleveland, Ohio), 10.4 μL 10 mM adenosine-5'-triphosphate (Boehringer Mannheim, Indianapolis, Ind.), and 2 μL polynucleotide kinase (30 units/μL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of equilibrated phenol (pH>8.0, United States Biochemical, Cleveland, Ohio) :chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 μL sterile water. The concentration was determined by measuring the absorbance of an aliquot of the DNA at 260 nm using 33 μg/mL for an absorbance of 1.0. Samples were stored at −20° C.

Example 9
Preparation of Uracil Templates used in Generation of Spleen Antibody Phage Libraries One mL of *E. Coli* CJ236 (BioRAD, Hercules, Calif.) overnight culture was added to 50 ml 2 x YT in a 250 mL baffled shake flask. The culture was grown at 37° C. to $OD_{600}$=0.6, inoculated with 10 μl of a 1/100 dilution of BS45 vector phage stock (described in co-pending, commonly assigned U.S. patent application Ser. No. 08/835,159, filed Apr. 4, 1997) and growth continued for 6 hr. Approximately 40 mL of the culture was centrifuged at 12 krpm for 15 minutes at 4° C. The supernatant (30 mL) was transferred to a fresh centrifuge tube and incubated at room temperature for 15 minutes after the addition of 15 μl of 10 mg/ml RNaseA (Boehringer Mannheim, Indianapolis, Ind.). The phage were precipitated by the addition of 7.5 ml of 20% polyethylene glycol 8000 (Fisher Scientific, Pittsburgh, Pa.)/ 3.5M ammonium acetate (Sigma Chemical Co., St. Louis, Mo.) and incubation on ice for 30 min. The sample was centrifuged at 12 krpm for 15 min at 2–8° C. The supernatant was carefully discarded, and the tube was briefly spun to remove all traces of supernatant. The pellet was resuspended in 400 μl of high salt buffer (300 mM NaCl, 100 mM Tris pH 8.0, 1 mM EDTA), and transferred to a 1.5 mL tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 μl sterile water and the concentration determined by $A_{260}$ using an absorbance of 1.0 for a concentration of 40 μg/ml. The template was diluted to 250 ng/μl with sterile water, aliquoted, and stored at −20° C.

Example 10
Mutagenesis of Uracil Template with ss-DNA and Electroporation into *E. coli* to Generate Antibody Phage Libraries Antibody phage display libraries were generated by simultaneously introducing single-stranded heavy and light chain genes onto a phage display vector uracil template. A typical mutagenesis was performed on a 2 μg scale by mixing the following in a 0.2 mL PCR reaction tube: 8 μl of (250 ng/μl) uracil template (Example 9), 8 μl of 10 x annealing buffer (200 mM Tris pH 7.0, 20 mM $MgCl_2$, 500 mM NaCl), 3.33 μl of kinased single-stranded heavy chain insert (100 ng/μl), 3.1 μl of kinased single-stranded light chain insert (100 ng/μl), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10 x synthesis buffer (5 mM each dNTP, 10 mM ATP, 100 mM Tris pH 7.4, 50 mM $MgCl_2$, 20 mM DTT), 8 μl T4 DNA ligase (1U/μl, Boehringer Mannheim, Indianapolis, Ind.), 8 μl diluted T7 DNA polymerase (1U/μl, New England BioLabs, Beverly, Mass.) and incubating at 37° C. for 30 min. The reaction was stopped with 300 μl of mutagenesis stop buffer (10 mM Tris pH 8.0, 10 mM EDTA).

The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μl of sterile water.

One μl mutagenesis DNA (500 ng) was transferred into 40 μl electrocompetent E. coli DH12S (Gibco/BRL, Gaithersburg, Md.) using the electroporation conditions in Example 11. The transformed cells were mixed with 1.0 mL 2×YT broth (Sambrook et al., supra) and transferred to 15 mL sterile culture tubes. The first round antibody phage was made by shaking the cultures overnight at 23° C. and 300 rpm. The efficiency of the electroporation was measured by plating 10 μl of $10^{-3}$ and $10^{-4}$ dilutions of the cultures on LB agar plates (see Example 15). These plates were incubated overnight at 37° C. The efficiency was determined by multiplying the number of plaques on the $10^{-3}$ dilution plate by $10^5$ or multiplying the number of plaques on the $10^{31\ 4}$ dilution plate by $10^6$. The overnight cultures from the electroporations were transferred to 1.5 ml tubes, and the cells were pelleted by centrifuging at 14 krpm for 5 min. The supernatant, which is the first round of antibody phage, was then transferred to 15 mL sterile centrifuge tubes with plug seal caps.

Example 11

Transformation of E. coli by Electroporation

The electrocompetent E. coli cells were thawed on ice. DNA was mixed with 20–40 μL electrocompetent cells by gently pipetting the cells up and down 2–3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the E. Coli Pulser (BioRAD, Hercules, Calif.) and electroporated with the voltage set at 1.88 kV according to the manufacturer's recommendations. The transformed sample was immediately diluted to 1 ml with 2×YT broth and processed as procedures dictated.

Example 12

Preparation of Biotinylated 29 kDa Antigen and Biotinylated Antibodies

The 29 kDa antigen was dialyzed against a minimum of 100 volumes of 20 mM borate, 150 mM NaCl, pH 8 (BBS) with 10 mM 2-mercaptoethanol at 2–8° C. for at least 4 hr. The buffer was changed at least once prior to biotinylation. Dithiothreitol (DTT) was added to a final concentration of 2 mM in the protein solution, which was incubated for 30 min at room temperature. The protein solution was passed through a GH-25 desalting column (Amicon, Beverly, Mass.) equilibrated with 50 mM potassium phosphate, 10 mM borate, 150 mM NaCl, 0.1 mM EDTA, pH 7.0, to remove the DTT and 2-mercaptoethanol. The protein was diluted to 0.1 mg/mL and split into fractions. One fraction was reacted with biotin-XX-NHS ester (Molecular Probes, Eugene, Oreg., stock solution at 100 mM in dimethylformamide) at a final concentration of 0.2 mM for 30 min at room temperature. A second fraction was reacted with 3-(N-maleimidylpropionyl)biocytin (Molecular Probes, Eugene, Oreg., stock solution at 100 mM in BBS, pH 8) at a final concentration of 0.1 mM for 30 min at room temperature. After 30 min, DTT (2 mM final concentration) was added to each reaction, and the NHS ester reaction was quenched by adding taurine (Aldrich Chemical Co., Milwaukee, Wis.) at a final concentration of 5 mM for 5 min. The protein solutions were extensively dialyzed into BBS with 1 mM DTT to remove unreacted small molecules. Biotin conjugates were stored at −70° C.

Monoclonal antibody EH29.Ab.13 was biotinylated using the following procedure. The antibody was dialyzed extensively into BBS, 1 mM 2-mercaptoethanol. The free cysteine at the end of the heavy chain constant region was reacted with N-ethyl maleimide (NEM, 1M in ethanol, Aldrich Chemical Co., Milwaukee, Wis.) by adding NEM to a final concentration of 20 mM and incubating 30 min at room temperature. After 30 min, the antibody was extensively dialyzed into BBS to remove the unreacted NEM. Biotin-XX-NHS ester was added to the antibody (final concentration of 0.5 mM) for 90 min at room temperature. The antibody was then extensively dialyzed into BBS to remove unreacted small molecules.

Example 13

Preparation of Alkaline Phosphatase-29 kDa Antigen Conjugate

Alkaline phosphatase (5 mg, AP, Calzyme Laboratories, San Luis Obispo, Calif.) was dissolved in 320 mL of column buffer (50 mM potassium phosphate, 10 mM borate, 150 mM NaCl, pH 7.0). The AP was passed through a GH25 column equilibrated in column buffer. The first 70% of the protein peak was collected. The AP concentration was determined to be 2.5 mg/mL by absorbance at 280 nm using an absorbance of 0.77 for a 1 mg/mL solution. The reaction of AP and succinimidyl 4-(N-maleimidomethyl) cyclohexane-1-carboxylate (SMCC, Pierce Chemical Co., Rockford, Ill.) was carried out using a 15:1 ratio of SMC-C:AP. SMCC was dissolved in acetonitrile at 60 mM and was added to AP while vortexing or rapidly stirring. The solution was allowed to stand at room temperature for 90 min before the unreacted SMCC and low molecular weight reaction products were separated from the AP using the GH25 column equilibrated with column buffer. 29 kDa antigen was dialyzed into phosphate buffered saline, pH 7.6 and 1 mM 2-mercaptoethanol. The buffer was changed at least once prior to use of the antigen. The amount of antigen was quantified by absorbance at 280 nm. DTT (2 mM final concentration) was added to 1.1 mg 29 kDa antigen (0.96 mL) and incubated at room temperature for 30 min in order to reduce the cysteine residues on the 29 kDa protein. After the incubation, the protein was passed through a GH25 column equilibrated in column buffer plus 0.1 mM EDTA. The 29 kDa antigen and AP-SMCC were mixed together using a 5:1 molar ratio of 29 kDa antigen:AP-SMCC and $MgCl_2$ was added to a final concentration of 4 mM. The reaction was allowed to proceed at room temperature for 2 hr, then overnight at 2–8° C.

The 29 kDa antigen-AP conjugate was purified by HPLC using a Hewlett Packard 1090 HPLC and a Zorbax GF-250 column (MAC-MOD Analytical, Inc., Chadds Ford, Pa.). The HPLC buffer was 0.2M ammonium sulfate, 0.05M potassium phosphate, 0.01M potassium borate, pH 7.0 and absorbance was measured at 280 nm. The collected conjugate was diluted into block containing 1% bovine serum albumin (from 30% BSA, Bayer, Kankakee, Ill.), 10 mM Tris, 150 mM NaCl, 1 mM $MgCl_2$, 0.1 mM $ZnCl_2$, 0.1% polyvinyl alcohol (80% hydrolyzed, Aldrich Chemical Co., Milwaukee, Wis.), pH 8.0, to a concentration of 70 μg/mL.

Example 14

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems, Framingham Mass.). While still separated by the magnet, the liquid was carefully removed from the magnetic latex using a 10 mL sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM TRIS, 150 mM NaCl, 20 mg/mL BSA, 0.1% Tween 20 (Fisher Scientific, Pittsburgh, Pa.), pH 7.5). The avidin magnetic latex needed for a panning experiment (200 µl/sample) was added to a sterile 15 ml centrifuge tube and brought to 10 ml with panning buffer. The tube was placed on the magnet for 10 min to separate the latex. The solution was carefully removed with a 10 mL sterile pipette as described above. The magnetic latex was resuspended in 10 mL of panning buffer to begin the second wash. The magnetic latex was washed a total of 3 times with panning buffer. After the final wash, the latex was resuspended in panning buffer to the starting volume.

Example 15

Plating M13 Phage or Cells Transformed with Antibody Phage-Display Vector Mutagenesis Reaction The phage samples were added to 200 µL of an overnight culture of *E. coli* XL1-Blue when plating on 100 mm LB agar plates or to 600 µl of overnight cells when plating on 150 mm plates in sterile 15 ml culture tubes. After adding LB top agar (3 mL for 100 mm plates or 9 mL for 150 mm plates, top agar stored at 55° C., Appendix A1, Sambrook et al., supra.), the mixture was evenly distributed on an LB agar plate that had been pre-warmed (37° C.–55° C.) to remove any excess moisture on the agar surface. The plates were cooled at room temperature until the top agar solidified. The plates were inverted and incubated at 37° C. as indicated.

Example 16

Developing Nitrocellulose Filters with Alkaline Phosphatase Conjugates

After overnight incubation of nitrocellulose filters on the LB agar plates, the filters were carefully removed from the plates with membrane forceps and incubated for 2 hr in either casein block (block with 1% casein (Hammersten grade, Research Organics, Cleveland, Ohio)), when using antigen-AP conjugates or block when using goat anti-mouse kappa-AP (Southern Biotechnology Associates, Inc, Birmingham, Ala.). After 2 hr, the filters were incubated with the AP conjugate for 2–4 hr. Antigen-AP conjugates were diluted into casein block at a final concentration of 1 µg/mL and goat anti-mouse kappa-AP conjugates were diluted into block at a final concentration of 1 µg/mL. Filters were washed 3 times with 40 mM TRIS, 150 mM NaCl, 0.05% Tween 20, pH 7.5 (TBST) (Fisher Chemical, Pittsburgh, Pa.) for 5 min each. After the final wash, the filters were developed in a solution containing 0.2 M 2-amino-2-methyl-1-propanol (JBL Scientific, San Luis Obispo, Calif.), 0.5 M TRIS, 0.33 mg/mL nitro blue tetrazolium (Fisher Scientific, Pittsburgh, Pa.) and 0.166 mg/mL 5-bromo-4-chloro-3-indolyl-phosphate, p-toluidine salt.

Example 17

Panning of Antibody Phage Libraries

The first round antibody phage was prepared as described in Example 10 using BS45 uracil template. Electroporations of mutagenesis DNA were performed yielding phage samples derived from different immunized mice. To create more diversity in the polyclonal library, each phage sample was panned separately. The antibody phage (about 0.9 mL) from each electroporation was transferred to a 15 mL disposable sterile centrifuge tube with plug seal cap. BSA (30 µL of 300 mg/mL solution) and 1 M Tris (50 µL, 1 M stock solution, pH 8.0) were added to each phage stock, followed by 5 µL $10^{-6}$ M 29 kDa antigen-biotin (maleimide reaction of Example 12) and 5 µL $10^{-6}$ M 29 kDa antigen-biotin (NHS ester reaction of Example 12). The antibody phage were allowed to come to equilibrium with the 29 kDa-biotin by incubating the phage at room temperature for 2 hr.

After the incubation, the phage samples were panned with avidin magnetic latex. The equilibrated avidin magnetic latex (see Example 14), 200 µL latex per sample, was incubated with the phage for 10 min at room temperature. After 10 min, approximately 9 mL of panning buffer was added to each phage sample, and the magnetic latex was separated from the solution using a magnet. After a ten minute separation, the unbound phage were carefully removed with a 10 mL sterile pipette. The magnetic latex was then resuspended in 10 mL of panning buffer to begin the second wash. The latex was washed a total of four times as described above. For each wash, the tubes were in contact with the magnet for 10 min to separate unbound phage from the magnetic latex. After the fourth wash, the magnetic latex was resuspended in 1 mL of panning buffer and transferred to a 1.5 mL tube.

The entire amount of magnetic latex for each sample was then resuspended in 200 µL 2YT and was plated on 150 mm LB plates as described in Example 15. The 150 mm plates were used to amplify the phage binding to the magnetic latex to generate the next round of antibody phage. These plates were incubated at 37° C. for 4 hr, then overnight at 20° C. After the overnight incubation, the second round antibody phage was eluted from the 150 mm plates by pipetting 10 mL 2YT media onto the lawn and gently shaking the plate at room temperature for 20 min. The phage samples were transferred to 15 mL disposable sterile centrifuge tubes with plug seal cap, and the debris from the LB plate was pelleted by centrifuging the tubes for 15 min at 3500 rpm. The second round antibody phage was then transferred to a new tube.

The second round of panning was set up by diluting 100 µL of each phage stock into 900 µL panning buffer and 10 µL 10 mM DTT in 15 mL disposable sterile centrifuge tubes with plug seal cap. The 29 kDa antigen-biotin mixture (10 µl at $10^{-7}$ M) was added to each sample, and the phage samples were incubated overnight at 2–8° C. The phage samples were panned with avidin magnetic latex following the overnight incubation as described above. After washing the latexes with panning buffer, each latex was plated on 150 mm LB agar plates. The plates were incubated at 37° C. for 4 hr, then overnight at 20° C.

After the second round of panning to 29 kDa-biotin, the antibody phage was subject to a round of enrichment for polyvalent display. Enrichment was effected by binding of the hexahistidine tag fused to the displayed heavy chain to NiNTA agarose (Qiagen Inc., Chatsworth, Calif.). The third round antibody phage (2.5 mL) were diluted into 2.5 mL panning buffer in 15 mL disposable sterile centrifuge tubes with plug seal cap. The NiNTA was equilibrated into panning buffer using the following procedure. The resin (1 mL per phage sample) was diluted to 50 mL with panning buffer in a 50 mL disposable sterile centrifuge tube with plug seal cap and then was pelleted in an IEC centrifuge at 500 rpm for 1 min. The supernatant was carefully removed with a 50 mL disposable pipette, after which the resin was again diluted to 50 mL with panning buffer for the second wash. The resin was washed in this manner a total of four times in order to equilibrate the resin in panning buffer. The equilibrated resin was then resuspended to its original volume with panning buffer.

Equilibrated resin (1 mL) was then added to the phlage, and the tube was gently rocked for 15 min. After 15 min, the resin was pelleted in an IEC centrifuge at 500 rpm for 1 min. The supernatant was gently removed with a 10 mL disposable pipette, and the resin was resuspended in 10 mL panning buffer for the first wash. The resin was pelleted as described above, the supernatant was removed, and the resin was resuspended a 2nd time in 10 mL panning buffer. This procedure was repeated for a total of five panning buffer washes.

After the final wash, the antibody phage was eluted by adding 0.8 mL 300 mM imidazole (Fisher Scientific, Pittsburgh, Pa.) in panning buffer to each sample, and rocking the tubes for 10 min at room temperature. The resin was pelleted by centrifuging the tubes at 14 krpm for 5 min at room temperature, and the phage were carefully transferred to new tubes. Each phage sample was diluted to about 1.1 mL with panning buffer, then 1 mL of each sample was transferred to a 15 mL disposable sterile centrifuge tube with a plug seal cap. The 29 kDa antigen-biotin (10 $\mu$l at $10^{-7}$ M) was added to each sample, and the phage samples were incubated overnight at 2–8° C.

After the overnight incubation, the phage were panned with avidin magnetic latex. After washing, each latex sample was resuspended in 1 mL panning buffer. Aliquots of each latex sample were taken at this point to plate on 100 mm LB agar plates to determine the percentage of kappa positives or functional positives. The majority of latex from each panning (99%) was plated on 150 mm LB agar plates to amplify the phage binding to the latex (see above). The 100 mm LB agar plates were incubated at 37° C. for 6–7 hr, then the plates were transferred to room temperature and nitrocellulose filters (pore size 0.45 mm, BA85 Protran, Schleicher and Schuell, Keene, N.H.) were overlaid onto the plaques. Plates with nitrocellulose filters were incubated overnight at room temperature. After the overnight incubation, the fourth round antibody phage was eluted from the 150 mm plates, and the filters were developed with 29 kDa-alkaline phosphatase or goat anti-mouse kappa alkaline phosphatase as described in Example 16.

Rounds of panning individual phage samples was continued as described in the preceding paragraph until the percentage of functional positives by plaque lift was greater than 70%.

Example 18

Selection of Anti-29 kDa Antigen Monoclonal Antibodies

Functional positive plaques were arbitrarily picked from phage samples following the third round of panning (described in Example 17) and individually transferred to sterile 15 ml culture tubes containing 2.75 ml of 2xYT and 0.25 ml of *Escherichia coli* strain XL1-Blue overnight culture. After overnight incubation at 300 rpm and 37° C., 1.5 ml of culture was transferred to an Eppendorf tube and centrifuged at 14 krpm for 5 min. The supernatant was transferred to a fresh tube and stored at 4° C. These monoclonals were amplified and subcloned with a cysteine residue at their carboxy terminus using PCR primers D and E (Table 1). In this case, a single 100 $\mu$l PCR reaction was performed using the phage stock as template. The PCR products were purified from a low melt agarose gel, digested with T4 DNA polymerase and annealed to pBRncoH3 as described in Example 18 of copending, commonly assigned U.S. patent application Ser. No. 08/835,159. The annealed DNA was diluted 1:4 in distilled water and one $\mu$l electroporated (Example 11) into 20 $\mu$l of electrocompetent *E. coli* strain, DH10B. The transformed cells were diluted to 1.0 ml with 2xYT broth and aliquots of the cells were plated on LB agar plates supplemented with tetracycline at 10 $\mu$g/ml. After overnight incubation at 37° C., colonies were picked from the plates and grown in 2xYT (10 mg/ml tetracycline) at 37° C., 300 rpm in sterile 15 mL culture tubes. The following day, glycerol freezer stocks were made from the cultures for long term storage at –80° C. Monoclonal antibodies were expressed and purified as in Example 4.

Monoclonal antibodies were assayed for binding to 29 kDa antigen-alkaline phosphatase. Each antibody was serially diluted 1:2 to a final dilution of 1:2048. The 29 kDa AP conjugate was diluted to about 1 $\mu$g/mL. Fifty $\mu$L of each diluted antibody was added to a conical bottom 96 well microtiter plate (Dynatech Laboratories, Inc., Chantilly, Va.) followed by 50 $\mu$L of the diluted AP conjugate to each antibody containing well. The plate was incubated at room temperature for 20 min. Fifty $\mu$L of equilibrated goat anti-mouse Fab-magnetic latex (Example 19) was added to each well for 10 min at room temperature. The plate was placed on a magnetic plate (PerSeptive Biosystems, Framingham Mass.) to separate the latex. The supernatant (25 $\mu$L) from each well was transferred to a new 96 well plate, and 200 $\mu$L of phenolphthalein monophosphate (6 mg/mL, JBL Scientific Inc., San Luis Obispo, Calif.) in 0.5M Tris, 0.2M 2-amino-2-methyl-1-propanol (JBL Scientific Inc., San Luis Obispo, Calif.), pH 10.2, was added. The kinetic signal was read immediately at 560 nm using a microplate reader (Molecular Devices, Sunnyvale, Calif.). A monoclonal antibody exhibiting good expression levels and high apparent affinity towards 29 kDa-alkaline phosphatase, EH29.Ab.13, was used to make a complementary polyclonal as described below in Example 20. This antibody was biotinylated as described in Example 12.

Example 19

Preparation of Goat anti-mouse Fab Magnetic Latex

The magnetic latex (Estapor, 10% solids, Bangs Laboratories, Fishers, Ind.) was thoroughly resuspended and 4 ml aliquoted into a 50 ml conical tube. The magnetic latex was suspended in 36 ml distilled water and separated from the solution for 10 min using a magnet. While still in the magnet, the liquid was carefully removed with a 50 mL sterile pipette. This washing process was repeated an additional three times. After the final wash, the latex was resuspended in 4 ml of distilled water. In a separate 50 ml conical tube, goat anti-mouse Fab (Antibodies Inc., Davis, Calif.) was diluted to 0.333 mg/mL in 0.1M morpholinoethanesulfonic acid (Fisher Scientific, Pittsburgh, Pa.), pH 5.5 to a volume of 36 mL. While vortexing, the 4 ml of washed magnetic latex was added to the diluted antibody and the mixture vortexed an additional 30 seconds. This mixture was incubated at 45° C. for 2 hr, shaking every 30 minutes. The magnetic latex was separated from the solution using a magnet and washed once with 40 ml PBS plus 1% BSA, once with PBS, and twice with BBS as described above. After the final wash, the latex was resuspended in 40 ml BBS and stored at 4° C. Immediately prior to use, the goat anti-mouse Fab magnetic latex was equilibrated in block as described in Example 14 for the avidin magnetic latex.

Example 20

Selection and Cloning of Complementary Polyclonal Antibody

The individual antibody phage samples from Example 17 were titered by plating 10 μl of a $10^{-7}$ dilution of each sample on LB agar plates. The phage stocks were then pooled using an equal number of phage from each sample. The phage sample was subjected to a round of enrichment by binding, and then eluting from NiNTA as described above. The eluted sample (1.0 ml) was transferred to a 15 ml disposable sterile centrifuge with plug seal cap and 10 μl of 10 mM DTT was added. Biotinylated anti-29 kDa antigen monoclonal antibody (EH29.Ab.13, 11 μl at $10^{-6}$M) from Example 18 and 29 kDa antigen (11 μl at $10^{-8}$ M) were mixed and incubated for 10 min at room temperature. Twenty μl of antibody-biotin/antigen was added to the phage sample, and the sample was incubated overnight at 4° C. The sample was panned with avidin magnetic latex and plated, including an aliquot from the final 1 ml wash to determine the percentage of functional positives, as described above. After overnight incubation, the first round complementary antibody phage were eluted from the 150 mm plates, and the filters developed with 29 kDa-alkaline phosphatase as described in Example 16. It was determined that the sample had 81% functional positives.

The first round complementary antibody phage sample was panned a second time as described above. The second round complementary antibody phage were eluted and stored at 4° C. The nitrocellulose filter was developed with 29 kDa-alkaline phosphatase as described above and the sample found be 90% functional positives. The second round of complementary polyclonal antibody phage selected to monoclonal EH29.Ab. 13 was subcloned into pBRncoH3 generally as described in Example 18 of Ser. No. 08/835, 159, filed Apr. 4, 1997. The subcloned polyclonal was designated EH29.Ab.32.PC. The polyclonal was conjugated to alkaline phosphatase as described in Example 22.

Example 21

Microtiter Plate Assay Sensitivity

The sensitivity of the monoclonal/polyclonal antibody pair was determined by performing a sandwich assay using biotinylated monoclonal antibody and alkaline phosphatase conjugated polyclonal antibody. Assays can be performed with streptavidin coated plates such as Reacti-Bind Streptavidin coated polystyrene 96 well plates (Pierce Chemical, Rockford, Ill.). After washing the 96 well plate with a plate washer like the Skan Washer (Skatron Instruments, Sterling, Va.), biotinylated monoclonal (EH29.Ab. 13, 50 μL of 2.5 μg/mL diluted in block) was added to 12 wells. The plate was incubated at room temperature for 1 hr. The plate was washed, then purified 29 kDa antigen (50 μL) was added in duplicate to the biotinylated monoclonal wells at 5 different concentrations of antigen, 0.5 ng/mL, 1.0 ng/mL, 2.0 ng/mL, 4.0 ng/mL and 6.0 ng/mL, and block was added to the last two wells for the blank. Antigen was incubated for 1 hr at room temperature, then the plate was washed. The complementary polyclonal alkaline phosphatase conjugate (EH29.Ab.32.PC, 50 μL of 2.5 μg/mL diluted in block) was added and incubated at room temperature for 1 hr. After 1 hr, the plate was washed and developed using the ELISA Amplification System (Gibco BRL, Gaithersburg, Md.) according to the manufacturer's instructions. The signal was read at 490 nm using a microplate reader (Molecular Devices, Sunnyvale, Calif.). Table 3 lists the signal at 490 nm versus the concentration of 29 kDa antigen.

TABLE 3 concentration of 29 kDa antigen versus signal at 490 nm (endpoint reading) for the antibody pair EH29.Ab.13/EH29.Ab.32.PC

| Concentration (ng/mL) | Absorbance (490 nm) |
| --- | --- |
| 0 | 0.049 |
| 0.5 | 0.318 |
| 1.0 | 0.534 |
| 2.0 | 0.893 |
| 4.0 | 1.599 |
| 6.0 | 1.903 |

Example 22

Preparation and Testing of Device for Detecting E. histolytica Infection

This Example describes the preparation and testing of an assay device for detecting E. histolytica infection. The assay method employs a recombinant polyclonal antibody to immobilize the 29 kDa antigen on a solid support, and a recombinant monoclonal antibody to detect the presence of immobilized 29 kDa antigen.

A. Preparation of antibody-alkaline phosphatase conjugates for use as detection reagents Detection reagents for use in an assay to detect E. histolytica infection were prepared by conjugating alkaline phosphatase to antibodies that bind to the E. histolytica 29 kDa antigen. The recombinant monoclonal antibody EH29.Ab. 13 (Example 18) was used to detect the 29 kDa antigen. Alkaline phosphatase (AP, Calzyme Laboratories, San Luis Obispo, Calif.) was dialyzed against a minimum of 100 volumes of column buffer (50 mM potassium phosphate, 10 mM borate, 150 mM NaCl, 1 mM $MgSO_4$, pH 7.0) at 2–8° C for a minimum of four hours and the buffer was changed at least twice prior to use of the AP. After the AP was removed from dialysis and brought to room temperature, the concentration was determined by determining the $A_{280}$, with an absorbance of 0.77 indicating a 1 mg/ml solution. The AP was diluted to 5 mg/ml with column buffer.

For crosslinking the AP to the antibody, AP was first linked to succinimidyl 4-(N-maleimidomethyl cyclohexane-1-carboxylate (SMCC, Pierce Chemical Co., Rockford Ill.) using a 20:1 ratio of SMCC:AP. SMCC was dissolved in acetonitrile at 20 mg/ml and diluted by a factor of 84 when added to AP while vortexing or rapidly stirring. The solution was allowed to stand at room temperature for 90 minutes before the unreacted SMCC and low molecular weight reaction products were separated from the AP using gel filtration chromatography (G-50 Fine, Pharmacia Biotech, Piscataway, N.J.) in a column equilibrated with column buffer.

Recombinant antibodies were reacted with 1 mM dithiothreitol (DTT, Calbiochem, San Diego, Calif.) for 30 minutes at room temperature to reduce a cysteine residue present near the carboxy terminus of the heavy chain constant region. The DTT was separated from the antibody by gel filtration chromatography using G50 Fine in column buffer without $MgSO_4$ but containing 0.1 mM ethylenediaminctetraacetic acid (EDTA, Fisher Scientific, Pittsburgh, Pa.). The AP and the antibody were mixed together in a molar ratio of 6 antibodies to one alkaline phosphatase and the conjugation reaction was allowed to continue for one hour at room temperature. To stop the conjugation, 2-mercaptoethanol was added to 1 mM final concentration to the conjugate solution and reacted for 5 minutes followed by the addition of N-ethyl maleimide to 2 mM final concentration. The conjugate was purified by gel filtration chromatography using SEPHACRYL™ S-200 HR (Pharmacia Biotech, Piscataway, N.J.). The free antibody was excluded from the conjugate pool which was diluted for use in immunoassays in a conjugate diluent containing 1% bovine serum albumin (from 30% BSA, Bayer, Kankakee. Ill.), 2% casein (Hammersten grade, Research Organics, Cleveland, Ohio), 100 mM trehalose (Aldrich Chemical Co., Milwaukee, Wis.), 50 mM potassium phosphate, 150 mM sodium chloride, 1 mM $MgSO_4$, 0.1 mM $ZnCl_2$, 0.1% polyvinyl alcohol (80% hydrolyzed, Aldrich Chemical Co., Milwaukee Wis.), pH 7.0.

B. Preparation of antibody-casein conjugates for use as capture reagents

Capture reagents for the 29 kDa antigen were prepared as follows. Where recombinant antibodies were used as capture reagents, the antibodies were first conjugated to casein. Casein was dissolved in deionized water at 2.5% solids by stirring it at 37–45° C. while adding concentrated potassium hydroxide to keep the pH of the solution between 7 and 8. After the pH had stabilized at 7.0, the casein was diluted with deionized water to a final $A_{280}$ of 10. The casein solution was subjected to tangential flow filtration through an ultrafiltration membrane with a molecular weight cut-off of 300,000 in order to exclude aggregated protein from the filtrate. The casein filtrate was concentrated to a final $A_{280}$ of approximately 10 by ultrafiltration.

A solution of SMCC was prepared at 20 mg/ml (60 mM) in acetonitrile and was diluted into the casein solution to a final concentration of 2 mM SMCC. The solution was allowed to stand for 90 minutes at room temperature and then was subjected to gel filtration chromatography in a column containing G50 Fine equilibrated in column buffer in order to separate the protein from the reactants. The casein was mixed with recombinant antibody EH29.Ab.32.PC that had been reacted with 1 mM DTT and subjected to gel filtration chromatography to remove the DTT as described in Example 22A above. The antibody was mixed with the casein in a 4:1 molar ratio and the reaction was allowed to proceed for one hour at room temperature before the conjugation was stopped as described above. The conjugate solution was subjected to gel filtration chromatography in a column containing SEPHACRYL™ S-200 HR in order to separate the conjugated antibody from the unconjugated antibody. The conjugated antibody was concentrated using an ultrafiltration membrane and subjected to dialysis vs. borate-buffered saline (BBS, 20 mM borate, 150 mM sodium chloride, 0.02% sodium azide, pH 8.2) and stored in BBS until immobilization on nylon membranes.

C. Preparation of assay devices

The assays were performed using capture reagents that were immobilized on nylon membranes. Recombinant Fab antibodies were conjugated to casein as described above prior to immobilization. The antibodies were immobilized on the nylon membranes (5 µm pore size; IMMUNODYNE™, Pall Corporation, Glen Cove, N.Y.) in a continuous process by pumping an antibody solution directly onto the membrane while the membrane was moved past a stationary nozzle which dispensed the antibody solution at a flow rate controlled by the pump. The antibody solution typically contained antibody at a concentration between 1 and 5 mg/ml in a buffer containing 20 mM borate, 150 mM sodium chloride, 0.02% sodium azide, and 10% trehalose, pH 8.2.

Each antibody was immobilized in a line approximately 0.040 inches wide, such that approximately 36 µL of antibody solution was required per linear foot of membrane. The antibody solution applied to the membrane was dried prior to blocking the entire membrane by saturating it with a solution containing 2% casein, 40% STABILICOAT™ (Bio-metric Systems, Eden Prairie, Minn.), 0.25% TRITON X-100™ (Sigma Chemical Co., St. Louis, Mo.) and drying the membrane in a drying tunnel or in a dry room. The antibody can also be applied in spots by applying a volume of approximately 1 µL of antibody solution to the membrane at the desired location prior to blocking and drying the membrane. Generally, several lines of immobilized antibody were placed on a membrane in this manner and the membrane was cut perpendicular to the direction of the antibody lines for placement in the assay devices.

Figure 1A:
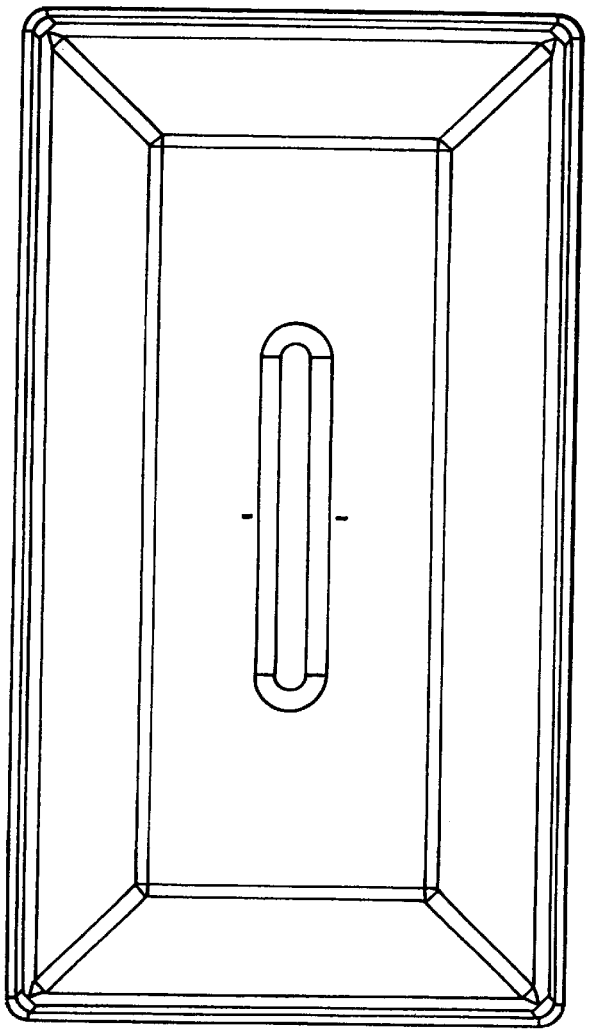
Figure 1B:
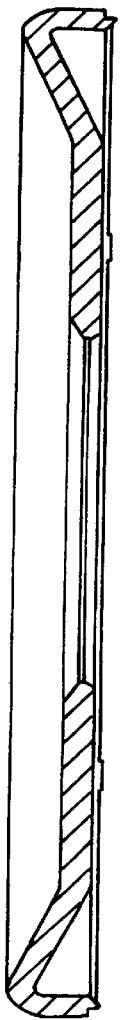
Figure 2A:
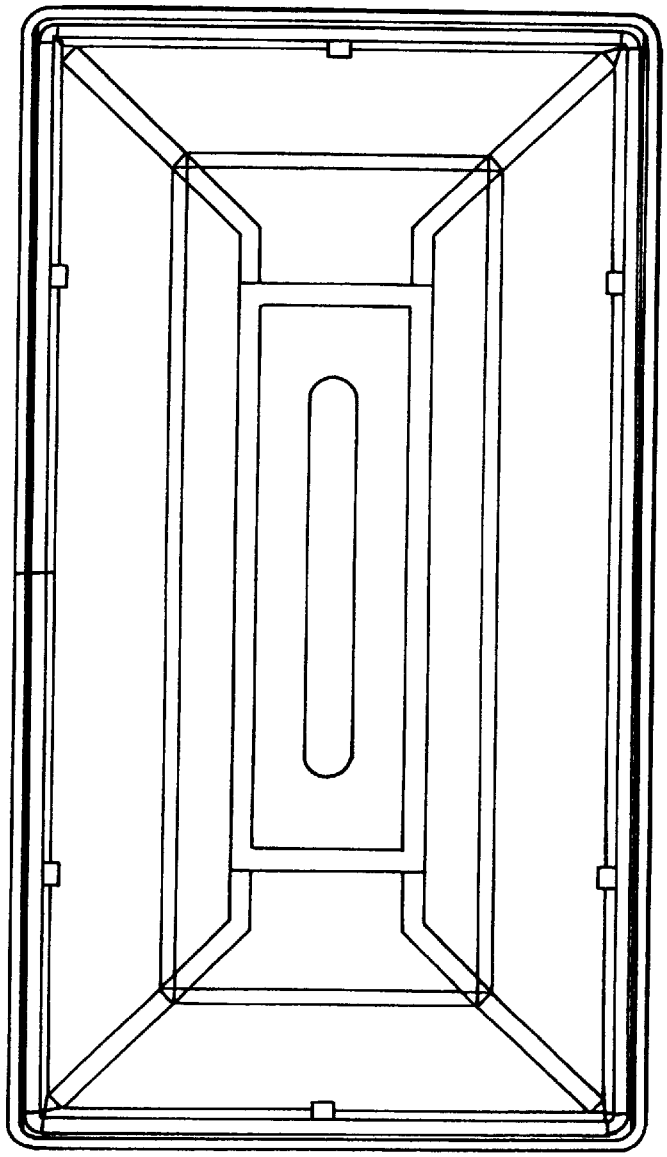
FIGS. 2A–C show a bottom piece of an apparatus for performing an immunoassay for detecting *E. histolytica* infection in a sample.
Figure 2B:
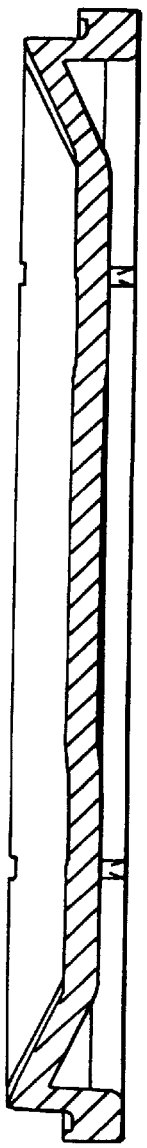
Figure 2C:
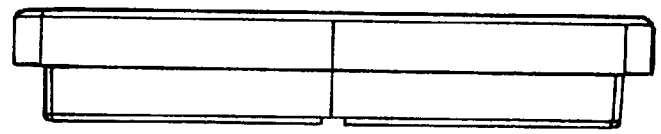

The cut membrane pieces were ultrasonically welded to an opening in a plastic device top (see FIG. 1A—top view, FIG. 1B—side section, and FIG. 1C—end view) which was then ultrasonically welded to a plastic bottom piece (see FIG. 2A—top view, FIG. 2B—side section, and FIG. 2C—end view) having grooves cut into its upper surface. The contact between the membrane and the two plastic pieces resulted in a network of capillary channels that caused fluids added to the membrane to flow through the membrane and into the capillary network between the two plastic pieces. Such devices are described in European Patent Application No. 447154.

For the immunoassay of the 29 kDa antigen, a total of three lines of antibody were immobilized on the membrane.

The top line in the device was a positive control for the immunoassay of the 29 kDa antigen. The antibody solution used in the immobilization step for the positive control contained the 29 kDa antigen at approximately 1 µg/ml mixed with the EH29.Ab.32.PC-casein conjugate at approximately 1 mg/ml. The next line on the membrane was for the capture and detection of the 29 kDa antigen. The solution used to immobilize the antibody for the 29 kDa antigen contained approximately 2 mg/ml of the EH29.Ab.32.PC antibody conjugated to casein. The last line of immobilized antibody on the device was a negative control line; the antibody solution used to apply this line to the membrane contained a recombinant polyclonal antibody (2 mg/ml) that was specific for an antigen not found in *E. histolytica*.

For filtering samples prior to performing the assays, disposable filter devices were constructed using standard 10-cc plastic syringes. Disks of filter material were cut to a diameter that would allow the disk to be placed into the barrel of the syringe so that sufficient contact was created between the syringe barrel and the edge of the filter disk. This prevented fluids from bypassing the filter material when liquid samples were forced through the filter by the plunger. At the bottom of the syringe closest to the outlet was a disk of glass fiber filter (GF/F, 0.7 µm, Whatman, Clifton, N.J.) followed by a disk of porous plastic (Porex Technologies, Fairburn, Ga.). The next two disks of filter material were both cut from CELLUPORE™ filter grade 850 material (Cellulo Co., Fresno, Calif.). The next disk of filter material was cut from CELLUPORE™ filter grade 315 material (Cellulo Co., Fresno, Calif.). The uppermost filter element in the syringe barrel was a bonded cellulose acetate material (American Filtrona, Richmond, Va.) that served as a prefilter for the filter elements described previously. An alternative filter device that contains essentially the same elements is the AUTOVIAL™ (Whatman, Clifton, N.J.) which is a disposable syringe that has a GMF glass fiber filter with a rating of 0.45 µm already connected to the end of the syringe. The other filter elements described above were placed in the barrel of the AUTOVIAL™ in the same order.

D. Immunoassay of the 29 kDa Antigen

Stool samples (approximately 0.5 g or 0.5 ml) were diluted tenfold with sample diluent containing 1% casein, 100 mM potassium phosphate, 150 mM sodium chloride, 0.1% Dow 193 surfactant (Dow Corning, Midland, Mich.), 0.1% bovine IgG (Sigma Chemical Co., St. Louis, Mo.), 0.1% sodium azide, pH 7.0, and then poured into the barrel of a filter device. The syringe plunger was inserted into the filter device and pressed down to expel the filtered sample through the end of the syringe into a tube. Using a disposable transfer pipet, 0.5 ml of sample was taken from the tube and transferred to the exposed membrane in the immunoassay device described above.

After the sample drained through the membrane in the device, the antibody EH29.Ab. 13 conjugated to alkaline phosphatase was applied in a volume of 140 µL and incubated for 3 minutes. The antibody conjugate was present at approximately 10 µg/ml. After the incubation, six drops of wash solution containing 100 mM tris (hydroxymethyl) aminomethane (TRIS, Fisher Scientific, Pittsburgh, Pa.), 150 mM sodium chloride, 0.5% Dow 193 surfactant, 0.1% sodium azide, and 20 mg/l of nitro blue tetrazolium (NBT) were applied from a dropper bottle. After the wash drained into the membrane, another six drops of wash solution were applied and allowed to drain. Three drops of substrate solution containing 10 mM indoxyl phosphate (JBL Scientific, San Luis Obispo, Calif.), 200 mM 2-amino-2-methyl-1-propanol (JBL Scientific, San Luis Obispo, Calif.), 500 mM TRIS, pH 10.2, were added from a dropper bottle and the device was incubated for five minutes at room temperature.

At the end of the incubation time, the presence of any visually detectable purple to black lines was noted. The positive control zone described above developed a clearly visible line that resulted from the binding of the antibody-alkaline phosphatase conjugate to the immobilized complex of antigen and antibody. Control samples containing the 29 kDa antigen spiked from purified preparations of recombinant protein to concentrations of 2 ng/ml or greater resulted in a visible line at the zone for the detection of this antigen. The negative control zone for the detection of non-specific binding of reagents developed a visible response for less than 1% of the clinical samples tested. When tested again using ¼ of the initial sample volume, no visible response was observed at the negative control zone for any of the samples.

E. Sensitivity of assay with purified antigen and cultured organisms

The purified recombinant antigen was serially diluted in a solution containing 1% bovine serum albumin, 10 mM 3-(N-morpholino)propanesulfonic acid (Fisher Scientific, Pittsburgh, Pa.), 150 mM sodium chloride, and 0.1% sodium azide, pH 7.0, and the dilutions were tested in replicates of ten using the same procedure employed with stool samples, a tenfold dilution of a 0.5-ml sample followed by filtration of the diluted sample. The lowest concentration of the antigen that consistently produced a positive visual response at the detection zone on the membrane was determined to be the limit of sensitivity of the assay. For the 29 kDa antigen, this was found to be 2 ng/ml.

Trophozoites of *E. histolytica* from strains 30459 and 30885 (American Type Culture Collection, Manassas, Va.) were cultured to a density of approximately $10^5$ cells/ml. The cultures were either diluted directly in sample diluent or subjected to sonication and diluted to determine the lowest concentration of cells that produced a positive result in the assay. For ATCC strain 30459, a positive result was obtained in the assay for samples containing as little as 170 organisms/ml. No difference was observed with or without sonication of the cells. For ATCC strain 30885, a positive result was observed in the assay for samples containing 600 organisms/ml or more and samples subjected to sonication could be detected by the assay at 60 organisms/ml. Culture isolates of *E. dispar* were also tested and produced positive results using the assay. The assay of the present invention does not distinguish between the Entamoeba species *histolytica* and *dispar* (see Diamond and Clark (1993) *J. Euk. Microbiol.* 40: 340–344). The traditional ova and parasite (O&P) examination using light microscopy and staining methods cannot distinguish these two species.

F. Clinical sensitivity and specificity of the assay

The clinical sensitivity and specificity of the assay was determined by testing 443 samples obtained from a patient population in Mexico and Peru. The results were compared to those obtained with a standard O&P examination and with a commercially available enzyme-labeled microtiter plate immunoassay (Alexon ProSpecT™ *Entamoeba histolytica* assay). Discrepancies between methods were resolved by comparing the three results for a discrepant sample. Since no method exists that can unequivocally identify the presence of the organism in samples, when two of the three methods produced the same result, that result was judged to be the correct result for that sample. Clinical sensitivity, specificity, positive predictive value and negative predictive value were calculated as described in the *Tietz Textbook of Clinical Chemistry* (second edition, page 496).

The results shown in Table 4 demonstrate that the TRIAGE® assay kit which employs the reagents described in this Example is more sensitive than the ova and parasite evaluation method that is traditionally used to detect *E. histolytica* detection. TRIAGE® is a registered trademark of Biosite Diagnostics Incorporated.

TABLE 4

Comparison of TRIAGE ® *E. histolytica* 29 kDa assay to Ova and Parasite Evaluation

|  |  | O & P Evaluation |  |  |
|---|---|---|---|---|
|  |  | + | - | Total |
| Triage® *E. histolytica/dispar* | + | 38 | 60 | 98 |
|  | - | 4 | 341 | 345 |
|  | Total | 42 | 401 | 443 |
| Sensitivity |  |  | 90.5% |  |
| Specificity |  |  | 85.0% |  |
| Positive Predictive Value |  |  | 38.8% |  |
| Negative Predictive Value |  |  | 98.8% |  |

The results in Table 5 demonstrate that the assay of the present invention was substantially equivalent to a commercially available immunoassay that detects an unspecified antigen or mixture of antigens. Results obtained when discrepancies among the tests were resolved are shown in Table 6.

TABLE 5

Comparison of TRIAGE ® *E. histolytica* 29 kDa assay to Alexon Assay

|  |  | Resolved |  |  |
|---|---|---|---|---|
|  |  | + | - | Total |
| Triage® *E. histolytica/dispar* | + | 94 | 4 | 98 |
|  | - | 10 | 335 | 345 |
|  | Total | 104 | 339 | 443 |
| Sensitivity |  |  | 90.4% |  |
| Specificity |  |  | 98.8% |  |
| Positive Predictive Value |  |  | 95.9% |  |
| Negative Predictive Value |  |  | 97.1% |  |

TABLE 6

Resolution of Discrepancies

|  |  | Resolved |  |  |
|---|---|---|---|---|
|  |  | + | - | Total |
| Triage® *E. histolytica/dispar* | + | 95 | 3 | 98 |
|  | - | 0 | 345 | 345 |
|  | Total | 95 | 348 | 443 |
| Sensitivity |  |  | 100.0% |  |
| Specificity |  |  | 99.1% |  |
| Positive Predictive Value |  |  | 96.9% |  |
| Negative Predictive Value |  |  | 100.0% |  |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of diagnosing infection of a mammal by an Entamoeba species, the method comprising:

contacting a stool sample obtained from the mammal with a capture reagent which binds to a 29 kDa antigen of *Entamoeba histolytica* or *Entamoeba dispar*, wherein the capture reagent forms a complex with the 29 kDa antigen if the 29 kDa antigen is present in the stool sample; and detecting whether 29 kDa antigen is bound to the capture reagent, wherein the presence of 29 kDa antigen is indicative of Entamoeba infection of the mammal.

2. The method of claim 1, wherein the capture reagent comprises an antibody which binds to 29 kDa antigen.

3. The method of claim 2, wherein the antibody is a recombinant antibody.

4. The method of claim 3, wherein the antibody is EH29.Ab.32.PC.

5. The method of claim 1, wherein the capture reagent is immobilized on a solid support.

6. The method of claim 5, wherein the capture reagent is immobilized on the solid support prior to contacting the capture reagent with the stool sample.

7. The method of claim 1, wherein the detection of the 29 kDa antigen is performed by contacting the 29 kDa antigen with a detection reagent which binds to the 29 kDa antigen.

8. The method of claim 7, wherein the detection reagent comprises an antibody which binds to 29 kDa antigen.

9. The method of claim 7, wherein the detection reagent comprises a detectable label.

10. The method of claim 9, wherein the detectable label is selected from the group consisting of a radioactive label, a fluorophore, a dye, an enzyme, and a chemilumenscent label.

11. The method of claim 1, wherein the capture reagent is recombinant polyclonal antibody preparation EH29.Ab.32.PC.

12. A kit for diagnosing infection of a mammal by an Entamoeba species, the kit comprising:

a solid support upon which is immobilized a capture reagent which binds to a 29 kDa antigen of *Entamoeba histolytica*; and a detection reagent which binds to the 29 kDa antigen;

wherein the capture reagent is selected from the group consisting of a) monoclonal antibody EH29.Ab. 13, and b) recombinant polyclonal antibody preparation EH29.Ab.32.PC.

13. The kit according to claim 12, wherein the kit further comprises a positive control that comprises a 29 kDa antigen.

14. A monoclonal antibody that specifically binds to 29 kDa antigen of *E. histolytica*, wherein the monoclonal antibody is EH29.Ab.13.

15. A recombinant polyclonal antibody preparation that specifically binds to 29 kDa antigen of *E. histolytica*, wherein the antibody preparation is EH29.Ab.32.PC.

* * * * *

UNITED STATES PATENT AND TRADEMARK OFFICE
CERTIFICATE OF CORRECTION

| | | |
|---|---|---|
| PATENT NO. | : 6,207,395 B1 | Page 1 of 1 |
| APPLICATION NO. | : 09/158347 | |
| DATED | : March 27, 2001 | |
| INVENTOR(S) | : Joseph Buechler et al. | |

It is certified that error appears in the above-identified patent and that said Letters Patent is hereby corrected as shown below:

In item (75) on the face page of the patent:

Please change Inventor name "Joe Buechler" to -- Joseph Buechler --.

Signed and Sealed this

Sixteenth Day of September, 2008

JON W. DUDAS
*Director of the United States Patent and Trademark Office*